United States Patent [19]
Gimbrone, Jr. et al.

[11] Patent Number: 5,708,147
[45] Date of Patent: Jan. 13, 1998

[54] MONONUCLEAR LEUKOCYTE DIRECTED ENDOTHELIAL ADHESION MOLECULE ASSOCIATED WITH ATHEROSCLEROSIS

[75] Inventors: Michael A. Gimbrone, Jr., Boston; Myron I. Cybulsky, Allston; Tucker Collins, Cohasset, all of Mass.

[73] Assignee: Brigham & Women's Hospital, Boston, Mass.

[21] Appl. No.: 261,304

[22] Filed: Jun. 16, 1994

Related U.S. Application Data

[63] Continuation of Ser. No. 649,565, Feb. 1, 1991, abandoned, which is a continuation-in-part of Ser. No. 487,038, Mar. 2, 1990, abandoned.

[51] Int. Cl.⁶ ................................................ C07K 14/00
[52] U.S. Cl. .................... 530/388.7; 530/350; 530/395; 436/63; 436/86
[58] Field of Search .................... 530/350, 388.7, 530/380, 395; 436/63, 86

[56] References Cited

U.S. PATENT DOCUMENTS 5,081,034  1/1992  Bevilacqua et al. .................... 435/252

FOREIGN PATENT DOCUMENTS

0408859A2  1/1991  European Pat. Off.
WO9013300  11/1990  WIPO.

OTHER PUBLICATIONS

Rosenfeld et al., *Arteriosclerosis* 7(1):9–23 (1987).
Ross, R., *New Engl. Journ. of Med.* 314(8):488–500 (1986).
Watanabe et al., *Lab. Invest.* 53(1):80–90 (1985).
Buja et al., *Arteriosclerosis* 3(1):87–101 (1983).
Berliner et al., *J. Clin. Invest.* 85:1260–1266 (1990).
Bevilacqua et al., *PNAS* 84:9238–9242 (1987).
Bevilacqua et al., *Science* 243:1160–1165 (1989).
Cotran et al., *J. Immunol.* 139:1883–1888 (1987).
Cotran et al., *J. Exp. Med.* 164:661–666 (1986).
Cybulski et al., *FASEB J.* 3:A1319 #6354 (1989).
Cybulski et al., *Am. J. Pathol.* 135:227–237 (1989).
Davies, *Lab. Invest.* 55:5–24 (1986).
DiCorleto et al., *J. Clin. Invest.* 75:1153–1161 (1985).
Dustin et al., *J. Immunol.* 137:245–254 (1986).
Elices et al., *Cell* 60:577–584 (1990).
Faggiotto et al., *Arteriosclerosis* 4:341–356 (1984).
Faggiotto et al., *Arteriosclerosis* 4:323–340 (1984).
Faull et al., *Transplant* 48:226–230 (1989).
Gerrity et al., *Arteriosclerosis* 5:55–66 (1985).
Gerrity et al., *Am. J. Pathol.* 103:191–200 (1981).
Gown et al., *Am. J. Pathol.* 125:191–207 (1986).
Gryglewski et al., *Hypertension* 12:530–548 (1988).
Hansson et al., *Arteriosclerosis* 9:567–578 (1989).
Hunkapiller et al., *Adv. In Immunol.* 44:1–63 (1989).
Joris et al., *Am. J. Pathol.* 113:341–358 (1983).
Klurfeld, *Arch. Pathol. Lab. Med.* 109:445–449 (1985).
Lewis et al., *Ann. NY Acad. Sci.* 454:91–100 (1985).
Libby, *Molecular Aspects of Medicine* 9:499–530 (1987).
Munro et al., *Lab. Invest.* 58:249–261 (1988).
Munro et al., *Am. J. Pathol.* 135:121–133 (1989).
Osborn et al., *Cell* 59:1203–1211 (1989).
Rice et al., *Science* 246:1303–1306 (1989).
Rice et al., *J. Exp. Med.* 171:1369–1374 (1990).
Schaffner et al., *Am. J. Pathol.* 100:57–73 (1980).
Simmons et al., *Nature* 331:624–627 (1988).
Smith et al., *J. Clin. Invest.* 83:2008–2017 (1989).
Springer, *Nature* 346:425–434 (1990).
Staunton et al., *Nature* 339:61–64 (1989).
Territo et al., *Arteriosclerosis* 9:824–828 (1989).
Young et al, Proc. Natl. Acad. Sci, USA, vol. 80, pp. 1194–1198, Mar. 1983.

*Primary Examiner*—Christine M. Nucker
*Assistant Examiner*—Laurie Scheiner
*Attorney, Agent, or Firm*—Sterne, Kessler, Goldstein & Fox

[57] ABSTRACT

The invention relates to novel endothelial cell-leukocyte adhesion molecules designated ATHERO-ELAM. ATHERO-ELAM molecules are expressed on cultured endothelial cells stimulated with bacterial LPS and selectively mediate the binding of monocytes to the endothelial cells. Monoclonal antibodies specific for ATHERO-ELAM bind to vascular endothelial cells involved in early atherosclerotic lesions, but not to vascular endothelial cells from uninvolved arterial tissue. ATHERO-ELAM and antibodies directed to ATHERO-ELAM may be used in identifying early atherosclerotic lesions and in treating and preventing atherosclerosis.

5 Claims, 23 Drawing Sheets

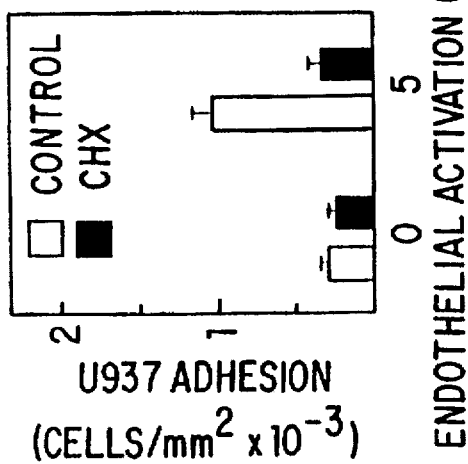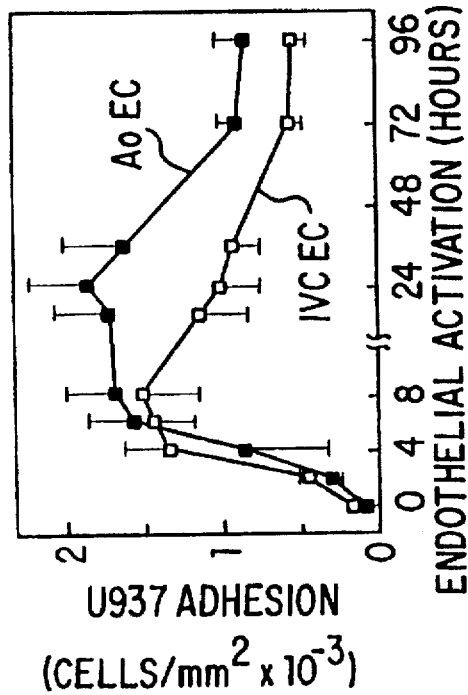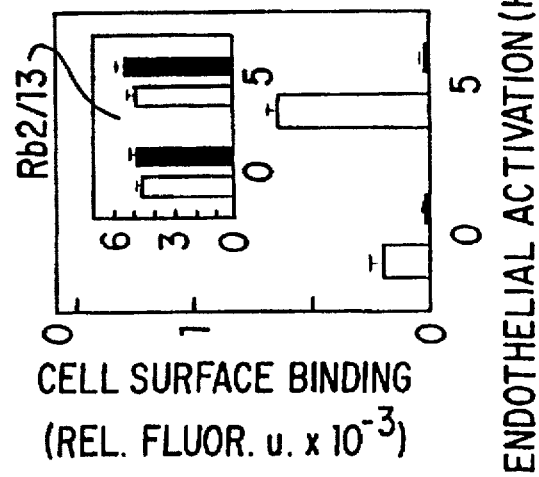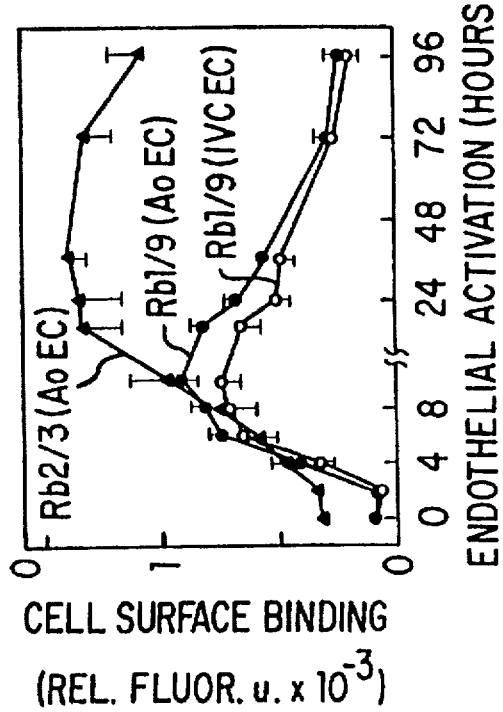

```
                            5    		   10		       15		    20
ATHERO-ELAM   F  K  I  E  T  F  P  E  S  R  S  L  A  Q  H  G  D  S  V  S  L  T
              |  |  |  |  |  |  |  |  |  |     |  |  |  |  |  |  |  |  |  |  |
VCAM-1        F  K  I  E  T  T  P  E  S  R  Y  L  A  Q  H  G  D  S  V  S  L  T
```

FIG. 6

```
ATGCCTGGGA  AGATGGTCCT  GGTCTTTGGA  GTCTCAACTC  TACTTTGGAT
GATGATTGCA  GCTTCTCAAG  CTTTTAAAAT  TGAGACCTTC  CCCGAATCCA  100
GATCTCTTGC  TCAAATTGGT  GACTCTGTCT  CATTGACTTG  CACCACCATG
GGCTGTGCAT  CCCCAACATT  CTCTTGGAGA  ACCCAGATAG  ACAGCCCACT  200
GAATGGGAAG  GTGAGGAGCG  AGGGACCAC   GTCCACATTG  ACCATGGATC
CTGTGAGTTT  CGAGAACGAA  CACTCTTACC  TGTGTACAGC  GACTTGTGAA  300
TCCAAGAAAC  TGGAAAAAGG  AGTTCAGGTG  GAAATCTACT  CATTCCCCAA
GGATCCAGAG  ATTCATTTGA  GTGGCCCTTT  GGAGGTTGGA  GAACCAATCA  400
CAGTCAAGTG  TTTGGTCCCT  GATGTATACC  CGTTTGATAG  GCTAGAAGTG
GATTTACTGA  AAGGTGACTA  CCTCATGAAG  AAACAGGACT  TTCTGGAAGA  500
CATGGACAGG  AAGTCCTTGG  AAACCAAGAG  TTTGGAAGTA  ACCTTTATTC
CAGTCATTGA  AGATATTGGA  AAACTTATTG  TTTGCCGAGC  TAAATTACAT  600
ATCGATGAAA  TTGATTCTGA  ACCCAAAGAA  AGAGAGACCA  CCAAAGAACT
ACAGGTCTAC  ATTCACCCA   AGAATACAGT  TATCTCTGTG  AATCCCTCCA  700
CAAGGCTGCA  AGAAGGTGGC  TCTGTGACAA  TGACATGTTC  CAGCGAGGGT
CTACCAGTTC  CAGAGATTTT  CTGGAGTAAG  AAACAAGATA  ATGGGAATCT  800
ACAGCGCCTT  TCTGGGAATG  CAACTCTCAC  ATTAATTGCT  ATGAGGATGG
```

FIG. 7A

```
AAGATTCTGG  AATTTATGTG  TGTGAAGGAG  TTAATCAGAT  TGGGAAAAGC   900
AGAAAGAGG   TGGAATTAAT  AGTTCAAGAG  AAACCATTTA  CCGTTGAGAT  1000
CTCCCCTGGA  CCCAGGATTG  CTCCTCAGAT  TGGGACCCA   GTTGTATTGA  1000
CATGTAGTGT  CAGGGGCTGT  GAGACCCCAT  CTTTCTCTTG  GAGAACCCAG
ATAGATAGCC  CTCTGAATGG  GCAGGTGACA  AGTGAAGGGA  CCAAGTCTTT  1100
GCTAACATTG  AGTCCTGTGA  GTTTTGAGAA  CGAAGATTCT  TACCTATGTA
CCGTGACCTG  TGGACATAAG  AAACTGGAAA  AGGGAATTCA  GGTGGAGCTC  1200
TACTCATTCC  CTAGAGATCC  AGAAATTGAG  CTGAGCGGTC  CACCAGTGAA
TGGCGCCCT   GTCACTGTCA  GCTGCAAAGT  TCCTAATGTG  TACCCTTTTG  1300
ACCGGTTGGA  GATTGAATTA  CTTAAGGGAG  AGACCATGAT  GAAGAATAAA
GAATTTTGG   AGGAAGAGGA  TAAGAAATCC  CTAGAGACCA  AAAGTTTAGA  1400
AATGACCTTC  ATCCCCACCA  TGGAAGACAC  TGGCCAAAGTT  CTGTTTGTC
AGGCCAAGTT  ACATATTGAT  GAAATGGAAT  TTGAACCCAA  ACAAAGGCAG  1500
AGTACACAAC  CACTTTTGT   CAATGTTGCC  CCCAGGGATA  TAGCTGTCTG
GGTCAGTCCC  TCGTCCATCG  TGGAGGAAGG  CCGTTCTGTG  AATATGACGT  1600
GCTCTAGTTA  TGGCCTTCCA  GCTCCAAAAA  TCCTGTGGAG  CAGACAACTG
```

FIG. 7B

```
AAAATGGGG ACCTACAGCC TCTTTCAGAA AATACAACTT TAGCCTTAAT 1700
TTCTACAAAA CTGGAAGATT CTGGTATTTA CGTGTGTGAA GGGATTAACC
TGGCTGGAAA GAGCAGAAAA GAAGTTGAAT TAGTTATCCA AGTTGCTCCA 1800
AAAGATATAC AACTGACGGC TTTCCTTCT AAGAGTGTCA AAGAAGGAGA
CACTGTCATT ATTCCCTGTA CTGTGGGAA TGTTCCTGAA ACTTGGATAA 1900
TTCTGAAGAA AAAAGCGGAG ACAGGAGACA CAGTGCTAAA GTCTATAGAT
GGTGCATATA CCATTCGTAA GGCCCAGCTG GAGGATGCAG GAGTGTATGA 2000
ATGAATCT AAAAATGAGG TTGGCTCACA ATTAAGAAGT ATAACACTTG
ATGTTAAAGT ACCTCCTCGA AACACGACAA TATCAATACA TCCATCTAGC 2100
AATGTTAAAG AAGGGAAAA TATCACAATT ACATGTAAAA CTTTAGTCA
TCCCCTGCA GTGATTATCC TGAAAAGAGT TGATCTTGCC AATGAAATTA 2200
CTATGTGTTC AAAGAATGGA ACATTACCT TATACCATGT CACTCAAAGT
GATACAGGGG TATATGTAAT CAGAGCTTCC AATGAGGTTG GGGATGATTC 2300
TGGACGGATT GAGATCTCAG TTATGAGAAG AGAAAATAGC AAGGACTATT
TTTCTCCTGA ACTTCTCGTG CTCTATTGTG CATCCTCCTT AATAATACCT 2400
GCCATCGGAA TGATCATTTA CTTTGCAAGA AAGCCAACA AGAAAGGATC
ACACAGTCTG GTAGAAGCAC AGAAATCAAA AGTGTAG              2487
```

FIG. 7C

```
MPGKMVLVFG VSTLLWMMIA ASQAFKIETF PESRSLAQIG DSVSLTCTTM
GCASPTFSWR TQIDSPLNGK VRSEGTTSTL TMDPVSFENE HSYLCTATCE   100
SKKLEKGVQV EIYSFPKDPE IHLSGPLEVG EPITVKCLVP DVYPFDRLEV
DLLKGDYLMK KQDFLEDMDR KSLETKSLEV TFIPVIEDIG KLIVCRAKLH   200
IDEIDSEPKE RETTKELQVY ISPKNTVISV NPSTRLQEGG SVTMTCSSEG
LPVPEIFWSK KQDNGNLQRL SGNATLTLIA MRMEDSGIYV CEGVNQIGKS   300
RKEVELIVQE KPFTVEISPG PRIAAQIGDP VVLTCSVRGC ETPSFSWRTQ
IDSPLNGQVT SEGTKSLLTL SPVSFENEHS YLCTVTCGHK KLEKGIQVEL   400
YSFPRDPEIE LSGPPVNGRP VTVSCKVPNV YPFDRLEIEL LKGETMMKNK
EFLEEEDKKS LETKSLEMTF IPTMEDTGKV LVCQAKLHID EMEFEPKQRQ   500
STQPLFVNVA PRDIAVWVSP SSIVEEGRSV NMTCSSYGLP APKILWSRQL
KNGDLQPLSE NTTLALISTK LEDSGIYVCE GINLAGKSRK EVELVIQVAP   600
KDIQLTAFPS KSVKEGDTVI ISCTCGNVPE TWIILKKKAE TGDTVLKSID
GAYTIRKAQL EDAGVYECES KNEVGSQLRS ITLDVKVPPR NTTISIHPSS   700
NVKEGENITI TCKTFSHPPA VIILKRVDLA NEITMCSKNG TFTLYHVTQS
DTGVYVIRAS NEVGDDSGRI EISVMRRENS KDYFSPELLV LYCASSLIIP   800
AIGMIIYFAR KANMKGSHSL VEAQKSKV                          828
```

FIG. 8

RABBIT: AGAAACCATT TACCGTTGAG ATCTCCCCTG GACCCAGGAT TGCTGCTCAG ATTGGGGACC

```
                 190        200        210        220        230        240
                  *          *          *          *          *          *
RABBIT:  TGAGTCCTGT GAGTTTTGAG AACGAACATT CTTACCTATG TACCCTGACC TGTGGACATA
HUMAN:   TGAGcCCTGT GAGTTTTGAG AACGAACACt CTTAtCTgTG cACaGTGACt TGTGGACATA 250        260        270
                  *          *          *
RABBIT:  AGAAACTGGA AAAGGGAATT CAGGTGGAGC TCTACT
HUMAN:   AGAAACTGGA AAAGGGAATc CAGGTGGAGC.TCTACT
```

FIG.9B

```
                                                                          150
ATCTTTCTCC TGGAGAACCC AGATAGACAG CCCTCTGAGC GGGAAGGTGA
 S  F  S    W  R  T  Q    I  D  S    P  L  S    G  K  V  R
                                                                          200
GGACTGAGGG GACCAATTCC ACGCTGACCC TGAGCCCTGT GAGTTTTGAG
 S  E  G    T  N  S    T  L  T  L    S  P  V    S  F  E
                                                                          250
AACGAACACT CTTATCTGTG CACACAGTGACT TGTGGACATA AGAAACTGGA
 N  E  H  S    Y  L  C    T  V  T    C  G  H  K  K  L  E
            276
AAAGGGAATC CAGGTGGAGC TCTACT
 K  G  I    Q  V  E  L    Y  T
```

FIG. 10B

```
1       FKIETTPESRYLAQIGDSVSLTCSTTGCESPFFSWRTQIDSPLNGK----------
        -----VTNEGTTS-TLTMNPVSFGNEHSYLCTATCESRKLEKGIQVEIY

2       SFPKDPEIHLSGPL-EAGKPITVKCSVA-DVYPFDRLEIDLLKGDHLMKSQE
        FLEDADRKSLETKSLEVTFTPVIEDIGKVLVCRAKLHIDEMDSVPTVRQAVKELQVY

3       ISPKNTVISVNPSTKL-QEGGSVTMTCSSEGLPAPEIFWSKKLDNGNLQH----------
        -----LS-GNATLTL-IAMRMEDSG-IYVCEGVNLIGKNRKEVELIVQ

AS-I    EKPFTVEISPGPRIAAQIGDSVMLTCSVMGCESPSFSWRTQIDSPLSGK----------
        -----VRSEGTNS-TLTLSPVSFENEHSYLCTVTCGHKKLEKGIQVELY

4       TFPRDPEIEMSGGL-VNGSSVTVSCKVP-SVYPLDRLEIEILLKGETILENIE
        FLEDTDMKSLENKSLEMTFIPTIEDTGKALVCQAKLHIDDMEFEPKQRSTQTLYVN

5       VAPRDTTVLVSPSSIL-EEGSSVNMTCLSQGFPAPKILWSRQLPNGELQP----------
        -----LS-ENATLTL-ISTKMEDSG-VYLCEGINQAGRSRKEVELIIQ

6       VTPKDIKLTAFPSESV-KEGDTVIISCTCGNVPETWIILKKAETGDTVL----------
        -----KS-IDGAYTI-RKAQLKDAG-VYECESKNKVGSQLRSLTLDVQ
```

FIG. 11

```
SP   HUMAN    MPGKMVVILGASNILWIMFAASQA
     RABBIT   MPGKMVLVFGVSTLLWMMIAASQA
                                 v
1             FKIETTPESRYLAQIGDSVSLTCSTTGCESPFFSWRTQIDSPLNGK------
              ----VTNEGTTS-TLTMNPVSFGNEHSYLCTATCESRKLEKGIQVELY
              FKIETFPESRSLAQIGDSVSLTCTTMGCASPTFSWRTQIDSPLNGK------
              ----VRSEGTTS-TLTMDPVSFENEHSYLCTATCESKKLEKGVQVELY

2             SFPKDPEIHLSGPL-EAGKPITVKCSVA-DVYPFDRLEIDLLKGDHLMKSQEF
              LEDADRKSLETKSLEVTFTPVIEDIGKVLVCRAKLHIDEMDSVPTVRQAVKELQVY
              SFPKDPEIHLSGPL-EVGEPITVKCLVP-DVYPFDRLEVDLLKGDYLMKKQDF
              LEDMDRKSLETKSLEVTFIPVIEDIGKLIVCRAKLHIDEIDSEPKERETTKELQVY

3             ISPKNTVISVNPSTKL-QEGGSVTMTCSSEGLPAPEIFWSKKLDNGNLQH------
              ----LS-GNATLTL-IAMRMEDSG-IYVCEGVNLIGKNRKEVELIVQ
              ISPKNTVISVNPSTRL-QEGGSVTMTCSSEGLPVPEIFWSKKQDNGNLQR------
              ----LS-GNATLTL-IAMRMEDSG-IYVCEGVNQIGKSRKEVELIVQ

AS-I          EKPFTVEISPGPRIAAQIGDSVMLTCSVMGCESPSFSWRTQIDSPLSGK------
              ----VRSEGTNS-TLTLSPVSFENEHSYLCTVTCGHKKLEKGIQVELY
              EKPFTVEISPGPRIAAQIGDPVVLTCSVRGCETPSFSWRTQIDSPLNGQ------
              ----VTSEGTKS-LLTLSPVSFENENHSYLCTVTCGHKKLEKGIQVELY
```

FIG. 14A

```
 4  HUMAN    TFPRDPEIEMSGGL-VNGSSVTVSCKVP-SVYPLDRLEIELLKGETILENIEF
    RABBIT   LEDTDMKSLENKSLEMTFIPTIEDTGKALVCQAKLHIDDMEFEPKQRQSTQLYVN
             SFPRDPEIELSGPP-VNGRPVTVSCKVP-NVYPFDRLEIELLKGETMMKNKEF
             LEEEDKKSLETKSLEMTFIPTMEDTGKVLVCQAKLHIDEMEFEPKQRQSTQPLFVN

5           VAPRDTTVLVSPSSIL-EEGSSVNMTCLSQGFPAPKILWSRQLPNGELQP------
             -----LS-ENATLTL-ISTKMEDSG-VYLCEGINQAGRSRKEVELIIQ
             VAPRDIAVWVSPSSIV-EEGRSVNMTCSSYGLPAPKILWSRQLKNGDLQP------
             -----LS-ENTTLAL-ISTKLEDSG-IYVCEGINLAGKSRKEVELVIQ

6           VTPKDIKLTAFPSESV-KEGDTVIISCTGGNVPETWIILKKKAETGDTVL------
             -----KS-IDGAYTI-RKAQLKDAG-VYECESKNKVGSQLRSLTLDVQ
             VAPKDIQLTAFPSKSV-KEGDTVIISCTGGNVPETWIILKKKAETGDTVL------
             -----KS-IDGAYTI-RKAQLEDAG-VYECESKNEVGSQLRSITLDVK

AS-III       VPPRNTTISIHPSSNV-KEGENITITCKTFSHPPAVIILKRVDLANEITM------
             ------CS-KNGTFTL-YHVTQSDTG-VYVIRASNEVGDDSGRIEISVM

TM/CYTO     GRENNKDVFSPELLVLYFASSLLIPAIGMIIYFARKANMKGSYSLVEAQKSKV
             RRENSKDYFSPELLVLYCASSLLIPAIGMIIYFARKANMKGSHSLVEAQKSKV
```

FIG. 14B

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 2487 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:1:

```
ATGCCTGGGA AGATGGTCCT GGTCTTTGGA GTCTCAACTC TACTTTGGAT      50
GATGATTGCA GCTTCTCAAG CTTTTAAAAT TGAGACCTTC CCCGAATCCA     100
GATCTCTTGC TCAAATTGGT GACTCTGTCT CATTGACTTG CACCACCATG     150
GGCTGTGCAT CCCCAACATT CTCTTGGAGA ACCCAGATAG ACAGCCCACT     200
GAATGGGAAG GTGAGGAGCG AGGGGACCAC GTCCACATTG ACCATGGATC     250
CTGTGAGTTT CGAGAACGAA CACTCTTACC TGTGTACAGC GACTTGTGAA     300
TCCAAGAAAC TGGAAAAAGG AGTTCAGGTG GAAATCTACT CATTCCCCAA     350
GGATCCAGAG ATTCATTTGA GTGGCCCTTT GGAGGTTGGA GAACCAATCA     400
CAGTCAAGTG TTTGGTCCCT GATGTATACC CGTTTGATAG GCTAGAAGTG     450
GATTTACTGA AAGGTGACTA CCTCATGAAG AAACAGGACT TTCTGGAAGA     500
CATGGACAGG AAGTCCTTGG AAACCAAGAG TTTGGAAGTA ACCTTTATTC     550
CAGTCATTGA AGATATTGGA AAACTTATTG TTTGCCGAGC TAAATTACAT     600
ATCGATGAAA TTGATTCTGA ACCCAAAGAA AGAGAGACCA CCAAAGAACT     650
ACAGGTCTAC ATTTCACCCA AGAATACAGT TATCTCTGTG AATCCCTCCA     700
CAAGGCTGCA AGAAGGTGGC TCTGTGACAA TGACATGTTC CAGCGAGGGT     750
CTACCAGTTC CAGAGATTTT CTGGAGTAAG AAACAAGATA ATGGGAATCT     800
ACAGCGCCTT TCTGGGAATG CAACTCTCAC ATTAATTGCT ATGAGGATGG     850
AAGATTCTGG AATTTATGTG TGTGAAGGAG TTAATCAGAT TGGGAAAGC      900
AGAAAGAGG TGGAATTAAT AGTTCAAGAG AAACCATTTA CCGTTGAGAT     950
CTCCCCTGGA CCCAGGATTG CTGCTCAGAT TGGGGACCCA GTTGTATTGA    1000
CATGTAGTGT CAGGGGCTGT GAGACCCCAT CTTTCTCTTG GAGAACCCAG    1050
ATAGATAGCC CTCTGAATGG GCAGGTGACA AGTGAAGGGA CCAAGTCTTT    1100
GCTAACATTG AGTCCTGTGA GTTTGAGAA CGAACATTCT TACCTATGTA    1150
CCGTGACCTG TGGACATAAG AAACTGGAAA AGGGAATTCA GGTGGAGCTC    1200
TACTCATTCC CTAGAGATCC AGAAATTGAG CTGAGCGGTC CACCAGTGAA    1250
TGGGCGCCCT GTCACTGTCA GCTGCAAAGT TCCTAATGTG TACCCTTTTG    1300
ACCGGTTGGA GATTGAATTA CTTAAGGGAG AGACCATGAT GAAGAATAAA    1350
GAATTTTTGG AGGAAGAGGA TAAGAAATCC CTAGAGACCA AAAGTTTAGA    1400
AATGACCTTC ATCCCCACCA TGGAAGACAC TGGCAAAGTT CTTGTTTGTC    1450
AGGCCAAGTT ACATATTGAT GAAATGGAAT TTGAACCCAA ACAAAGGCAG    1500
```

-continued

```
AGTACACAAC CACTTTTTGT CAATGTTGCC CCCAGGGATA TAGCTGTCTG  1550
GGTCAGTCCC TCGTCCATCG TGGAGGAAGG CCGTTCTGTG AAATATGACGT 1600
GCTCTAGTTA TGGCCTTCCA GCTCCAAAAA TCCTGTGGAG CAGACAACTG  1650
AAAAATGGGG ACCTACAGCC TCTTTCAGAA AATACAACTT TAGCCTTAAT  1700
TTCTACAAAA CTGGAAGATT CTGGTATTTA CGTGTGTGAA GGGATTAACC  1750
TGGCTGGAAA GAGCAGAAAA GAAGTTGAAT TAGTTATCCA AGTTGCTCCA  1800
AAAGATATAC AACTGACGGC TTTTCCTTCT AAGAGTGTCA AGAAGGAGA   1850
CACTGTCATT ATTTCCTGTA CTTGTGGGAA TGTTCCTGAA ACTTGGATAA  1900
TTCTGAAGAA AAAAGCGGAG ACAGGAGACA CAGTGCTAAA GTCTATAGAT  1950
GGTGCATATA CCATTCGTAA GGCCCAGCTG GAGGATGCAG GAGTGTATGA  2000
ATGTGAATCT AAAAATGAGG TTGGCTCACA ATTAAGAAGT ATAACACTTG  2050
ATGTTAAAGT ACCTCCTCGA AACACGACAA TATCAATACA TCCATCTAGC  2100
AATGTTAAAG AAGGGGAAAA TATCACAATT ACATGTAAAA CTTTTAGTCA  2150
TCCCCCTGCA GTGATTATCC TGAAAAGAGT TGATCTTGCC AATGAAATTA  2200
CTATGTGTTC AAAGAATGGA ACATTTACCT TATACCATGT CACTCAAAGT  2250
GATACAGGGG TATATGTAAT CAGAGCTTCC AATGAGGTTG GGATGATTC   2300
TGGACGGATT GAGATCTCAG TTATGAGAAG AGAAAATAGC AAGGACTATT  2350
TTTCTCCTGA ACTTCTCGTG CTCTATTGTG CATCCTCCTT AATAATACCT  2400
GCCATCGGAA TGATCATTTA CTTTGCAAGA AAAGCCAACA TGAAAGGATC  2450
ACACAGTCTG GTAGAAGCAC AGAAATCAAA AGTGTAG                2487
```

( 2 ) INFORMATION FOR SEQ ID NO:2:

( i ) SEQUENCE CHARACTERISTICS:
      ( A ) LENGTH: 828 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

```
Met Pro Gly Lys Met Val Leu Val Phe Gly Val Ser Thr Leu Leu Trp
 1               5                  10                  15

Met Met Ile Ala Ala Ser Gln Ala Phe Lys Ile Glu Thr Phe Pro Glu
                20                  25                  30

Ser Arg Ser Leu Ala Gln Ile Gly Asp Ser Val Ser Leu Thr Cys Thr
            35                  40                  45

Thr Met Gly Cys Ala Ser Pro Thr Phe Ser Trp Arg Thr Gln Ile Asp
        50                  55                  60

Ser Pro Leu Asn Gly Lys Val Arg Ser Glu Gly Thr Thr Ser Thr Leu
65                  70                  75                  80

Thr Met Asp Pro Val Ser Phe Glu Asn Glu His Ser Tyr Leu Cys Thr
                85                  90                  95

Ala Thr Cys Glu Ser Lys Lys Leu Glu Lys Gly Val Gln Val Glu Ile
            100                 105                 110

Tyr Ser Phe Pro Lys Asp Pro Glu Ile His Leu Ser Gly Pro Leu Glu
        115                 120                 125

Val Gly Glu Pro Ile Thr Val Lys Cys Leu Val Pro Asp Val Tyr Pro
    130                 135                 140

Phe Asp Arg Leu Glu Val Asp Leu Leu Lys Gly Asp Tyr Leu Met Lys
```

-continued

```
145                         150                         155                         160
Lys  Gln  Asp  Phe  Leu  Glu  Asp  Met  Asp  Arg  Lys  Ser  Leu  Glu  Thr  Lys
                    165                       170                       175

Ser  Leu  Glu  Val  Thr  Phe  Ile  Pro  Val  Ile  Glu  Asp  Ile  Gly  Lys  Leu
                    180                       185                       190

Ile  Val  Cys  Arg  Ala  Lys  Leu  His  Ile  Asp  Glu  Ile  Asp  Ser  Glu  Pro
               195                       200                       205

Lys  Glu  Arg  Glu  Thr  Thr  Lys  Glu  Leu  Gln  Val  Tyr  Ile  Ser  Pro  Lys
     210                       215                       220

Asn  Thr  Val  Ile  Ser  Val  Asn  Pro  Ser  Thr  Arg  Leu  Gln  Glu  Gly  Gly
225                       230                       235                       240

Ser  Val  Thr  Met  Thr  Cys  Ser  Ser  Glu  Gly  Leu  Pro  Val  Pro  Glu  Ile
                    245                       250                       255

Phe  Trp  Ser  Lys  Lys  Gln  Asp  Asn  Gly  Asn  Leu  Gln  Arg  Leu  Ser  Gly
                    260                       265                       270

Asn  Ala  Thr  Leu  Thr  Leu  Ile  Ala  Met  Arg  Met  Glu  Asp  Ser  Gly  Ile
               275                       280                       285

Tyr  Val  Cys  Glu  Gly  Val  Asn  Gln  Ile  Gly  Lys  Ser  Arg  Lys  Glu  Val
     290                       295                       300

Glu  Leu  Ile  Val  Gln  Glu  Lys  Pro  Phe  Thr  Val  Glu  Ile  Ser  Pro  Gly
305                       310                       315                       320

Pro  Arg  Ile  Ala  Ala  Gln  Ile  Gly  Asp  Pro  Val  Val  Leu  Thr  Cys  Ser
                    325                       330                       335

Val  Arg  Gly  Cys  Glu  Thr  Pro  Ser  Phe  Ser  Trp  Arg  Thr  Gln  Ile  Asp
                    340                       345                       350

Ser  Pro  Leu  Asn  Gly  Gln  Val  Thr  Ser  Glu  Gly  Thr  Lys  Ser  Leu  Leu
               355                       360                       365

Thr  Leu  Ser  Pro  Val  Ser  Phe  Glu  Asn  Glu  His  Ser  Tyr  Leu  Cys  Thr
     370                       375                       380

Val  Thr  Cys  Gly  His  Lys  Lys  Leu  Glu  Lys  Gly  Ile  Gln  Val  Glu  Leu
385                       390                       395                       400

Tyr  Ser  Phe  Pro  Arg  Asp  Pro  Glu  Ile  Glu  Leu  Ser  Gly  Pro  Pro  Val
                    405                       410                       415

Asn  Gly  Arg  Pro  Val  Thr  Val  Ser  Cys  Lys  Val  Pro  Asn  Val  Tyr  Pro
                    420                       425                       430

Phe  Asp  Arg  Leu  Glu  Ile  Glu  Leu  Leu  Lys  Gly  Glu  Thr  Met  Met  Lys
               435                       440                       445

Asn  Lys  Glu  Phe  Leu  Glu  Glu  Asp  Lys  Lys  Ser  Leu  Glu  Thr  Lys
     450                       455                       460

Ser  Leu  Glu  Met  Thr  Phe  Ile  Pro  Thr  Met  Glu  Asp  Thr  Gly  Lys  Val
465                       470                       475                       480

Leu  Val  Cys  Gln  Ala  Lys  Leu  His  Ile  Asp  Glu  Met  Glu  Phe  Glu  Pro
                    485                       490                       495

Lys  Gln  Arg  Gln  Ser  Thr  Gln  Pro  Leu  Phe  Val  Asn  Val  Ala  Pro  Arg
                    500                       505                       510

Asp  Ile  Ala  Val  Trp  Val  Ser  Pro  Ser  Ile  Val  Glu  Glu  Gly  Arg
               515                       520                       525

Ser  Val  Asn  Met  Thr  Cys  Ser  Ser  Tyr  Gly  Leu  Pro  Ala  Pro  Lys  Ile
     530                       535                       540

Leu  Trp  Ser  Arg  Gln  Leu  Lys  Asn  Gly  Asp  Leu  Gln  Pro  Leu  Ser  Glu
545                       550                       555                       560

Asn  Thr  Thr  Leu  Ala  Leu  Ile  Ser  Thr  Lys  Leu  Glu  Asp  Ser  Gly  Ile
                    565                       570                       575
```

```
Tyr Val Cys Glu Gly Ile Asn Leu Ala Gly Lys Ser Arg Lys Glu Val
            580                 585                 590

Glu Leu Val Ile Gln Val Ala Pro Lys Asp Ile Gln Leu Thr Ala Phe
        595                 600                 605

Pro Ser Lys Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
            645                 650                 655

Lys Ala Gln Leu Glu Asp Ala Gly Val Tyr Glu Cys Glu Ser Lys Asn
            660                 665                 670

Glu Val Gly Ser Gln Leu Arg Ser Ile Thr Leu Asp Val Lys Val Pro
        675                 680                 685

Pro Arg Asn Thr Thr Ile Ser Ile His Pro Ser Ser Asn Val Lys Glu
    690                 695                 700

Gly Glu Asn Ile Thr Ile Thr Cys Lys Thr Phe Ser His Pro Pro Ala
705                 710                 715                 720

Val Ile Ile Leu Lys Arg Val Asp Leu Ala Asn Glu Ile Thr Met Cys
            725                 730                 735

Ser Lys Asn Gly Thr Phe Thr Leu Tyr His Val Thr Gln Ser Asp Thr
            740                 745                 750

Gly Val Tyr Val Ile Arg Ala Ser Asn Glu Val Gly Asp Asp Ser Gly
        755                 760                 765

Arg Ile Glu Ile Ser Val Met Arg Arg Glu Asn Ser Lys Asp Tyr Phe
    770                 775                 780

Ser Pro Glu Leu Leu Val Leu Tyr Cys Ala Ser Ser Leu Ile Ile Pro
785                 790                 795                 800

Ala Ile Gly Met Ile Ile Tyr Phe Ala Arg Lys Ala Asn Met Lys Gly
            805                 810                 815

Ser His Ser Leu Val Glu Ala Gln Lys Ser Lys Val
            820                 825
```

(2) INFORMATION FOR SEQ ID NO:3:

(i) SEQUENCE CHARACTERISTICS:
(A) LENGTH: 276 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:3:

```
AGAAACCATT TACTGTTGAG ATCTCCCCTG GACCCCGGAT TGCTGCTCAG        50

ATTGGAGACT CAGTCATGTT GACATGTAGT GTCATGGGCT GTGAATCCCC       100

ATCTTTCTCC TGGAGAACCC AGATAGACAG CCCTCTGAGC GGGAAGGTGA       150

GGAGTGAGGG GACCAATTCC ACGCTGACCC TGAGCCCTGT GAGTTTTGAG       200

AACGAACACT CTTATCTGTG CACAGTGACT TGTGGACATA AGAAACTGGA       250

AAAGGGAATC CAGGTGGAGC TCTACT                                 276
```

(2) INFORMATION FOR SEQ ID NO:4:

(i) SEQUENCE CHARACTERISTICS:
(A) LENGTH: 92 amino acids
(B) TYPE: amino acid
(D) TOPOLOGY: linear ( i i ) MOLECULE TYPE: peptide ( i x ) FEATURE: Sequence ID No. 4 represents amino acids 310-401
of Sequence ID No. 2.

( x i ) SEQUENCE DESCRIPTION: SEQ ID NO:4:

| Glu | Lys | Pro | Phe | Thr | Val | Glu | Ile | Ser | Pro | Gly | Pro | Arg | Ile | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Ile | Gly | Asp | Pro | Val | Val | Leu | Thr | Cys | Ser | Val | Arg | Gly | Cys | Glu |
|     |     |     | 20  |     |     |     |     | 25  |     |     |     |     | 30  |     |     |

| Thr | Pro | Ser | Phe | Ser | Trp | Arg | Thr | Gln | Ile | Asp | Ser | Pro | Leu | Asn | Gly |
|     |     | 35  |     |     |     |     | 40  |     |     |     |     | 45  |     |     |     |

| Gln | Val | Thr | Ser | Glu | Gly | Thr | Lys | Ser | Leu | Leu | Thr | Leu | Ser | Pro | Val |
|     | 50  |     |     |     |     | 55  |     |     |     |     | 60  |     |     |     |     |

| Ser | Phe | Glu | Asn | Glu | His | Ser | Tyr | Leu | Cys | Thr | Val | Thr | Cys | Gly | His |
| 65  |     |     |     |     | 70  |     |     |     |     | 75  |     |     |     |     | 80  |

| Lys | Lys | Leu | Glu | Lys | Gly | Ile | Gln | Val | Glu | Leu | Tyr |
|     |     |     |     | 85  |     |     |     |     | 90  |     |     |

( 2 ) INFORMATION FOR SEQ ID NO:5:

( i ) SEQUENCE CHARACTERISTICS:
( A ) LENGTH: 92 amino acids
( B ) TYPE: amino acid
( D ) TOPOLOGY: linear ( i i ) MOLECULE TYPE: peptide ( i x ) FEATURE: Sequence ID No. 5 represents amino acids 286-377
of Sequence ID No. 7.

( x i ) SEQUENCE DESCRIPTION: SEQ ID NO:5:

| Glu | Lys | Pro | Phe | Thr | Val | Glu | Ile | Ser | Pro | Gly | Pro | Arg | Ile | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Ile | Gly | Asp | Ser | Val | Met | Leu | Thr | Cys | Ser | Val | Met | Gly | Cys | Glu |
|     |     |     | 20  |     |     |     |     | 25  |     |     |     |     | 30  |     |     |

| Ser | Pro | Ser | Phe | Ser | Trp | Arg | Thr | Gln | Ile | Asp | Ser | Pro | Leu | Ser | Gly |
|     |     | 35  |     |     |     |     | 40  |     |     |     |     | 45  |     |     |     |

| Lys | Val | Arg | Ser | Glu | Gly | Thr | Asn | Ser | Thr | Leu | Thr | Leu | Ser | Pro | Val |
|     | 50  |     |     |     |     | 55  |     |     |     |     | 60  |     |     |     |     |

| Ser | Phe | Glu | Asn | Glu | His | Ser | Tyr | Leu | Cys | Thr | Val | Thr | Cys | Gly | His |
| 65  |     |     |     |     | 70  |     |     |     |     | 75  |     |     |     |     | 80  |

| Lys | Lys | Leu | Glu | Lys | Gly | Ile | Gln | Val | Glu | Leu | Tyr |
|     |     |     |     | 85  |     |     |     |     | 90  |     |     |

( 2 ) INFORMATION FOR SEQ ID NO:6:

( i ) SEQUENCE CHARACTERISTICS:
( A ) LENGTH: 276 base pairs
( B ) TYPE: nucleic acid
( C ) STRANDEDNESS: double
( D ) TOPOLOGY: linear ( i i ) MOLECULE TYPE: DNA ( i x ) FEATURE: Sequence ID No. 6 represents nucleotides 929-1204
of Sequence ID No. 1.

( x i ) SEQUENCE DESCRIPTION: SEQ ID NO:6:

| AGAAACCATT | TACCGTTGAG | ATCTCCCCTG | GACCCAGGAT | TGCTGCTCAG | 50  |
|------------|------------|------------|------------|------------|-----|
| ATTGGGGACC | CAGTTGTATT | GACATGTAGT | GTCAGGGGCT | GTGAGACCCC | 100 |
| ATCTTTCTCT | TGGAGAACCC | AGATAGATAG | CCCTCTGAAT | GGGCAGGTGA | 150 |

```
CAAGTGAAGG GACCAAGTCT TTGCTAACAT TGAGTCCTGT GAGTTTTGAG      200

AACGAACATT CTTACCTATG TACCGTGACC TGTGGACATA AGAAACTGGA      250

AAAGGGAATT CAGGTGGAGC TCTACT                                276
```

( 2 ) INFORMATION FOR SEQ ID NO:7:

( i ) SEQUENCE CHARACTERISTICS:
        ( A ) LENGTH: 662 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Phe Lys Ile Glu Thr Thr Pro Glu Ser Arg Tyr Leu Ala Gln Ile Gly
 1           5                  10                  15

Asp Ser Val Ser Leu Thr Cys Ser Thr Thr Gly Cys Glu Ser Pro Phe
             20                  25                  30

Phe Ser Trp Arg Thr Gln Ile Asp Ser Pro Leu Asn Gly Lys Val Thr
             35                  40                  45

Asn Glu Gly Thr Thr Ser Thr Leu Thr Met Asn Pro Val Ser Phe Gly
 50                  55                  60

Asn Glu His Ser Tyr Leu Cys Thr Ala Thr Cys Glu Ser Arg Lys Leu
 65                  70                  75                  80

Glu Lys Gly Ile Gln Val Glu Ile Tyr Ser Phe Pro Lys Asp Pro Glu
                 85                  90                  95

Ile His Leu Ser Gly Pro Leu Glu Ala Gly Lys Pro Ile Thr Val Lys
                100                 105                 110

Cys Ser Val Ala Asp Val Tyr Pro Phe Asp Arg Leu Glu Ile Asp Leu
             115                 120                 125

Leu Lys Gly Asp His Leu Met Lys Ser Gln Glu Phe Leu Glu Asp Ala
130                 135                 140

Asp Arg Lys Ser Leu Glu Thr Lys Ser Leu Glu Val Thr Phe Thr Pro
145                 150                 155                 160

Val Ile Glu Asp Ile Gly Lys Val Leu Val Cys Arg Ala Lys Leu His
                165                 170                 175

Ile Asp Glu Met Asp Ser Val Pro Thr Val Arg Gln Ala Val Lys Glu
                180                 185                 190

Leu Gln Val Tyr Ile Ser Pro Lys Asn Thr Val Ile Ser Val Asn Pro
            195                 200                 205

Ser Thr Lys Leu Gln Glu Gly Gly Ser Val Thr Met Thr Cys Ser Ser
210                 215                 220

Glu Gly Leu Pro Ala Pro Glu Ile Phe Trp Ser Lys Lys Leu Asp Asn
225                 230                 235                 240

Gly Asn Leu Gln His Leu Ser Gly Asn Ala Thr Leu Thr Leu Ile Ala
                245                 250                 255

Met Arg Met Glu Asp Ser Gly Ile Tyr Val Cys Glu Gly Val Asn Leu
            260                 265                 270

Ile Gly Lys Asn Arg Lys Glu Val Glu Leu Ile Val Gln Glu Lys Pro
        275                 280                 285

Phe Thr Val Glu Ile Ser Pro Gly Pro Arg Ile Ala Ala Gln Ile Gly
    290                 295                 300

Asp Ser Val Met Leu Thr Cys Ser Val Met Gly Cys Glu Ser Pro Ser
305                 310                 315                 320

Phe Ser Trp Arg Thr Gln Ile Asp Ser Pro Leu Ser Gly Lys Val Arg
```

|     |     |     |     |     |     |     |     | 325 |     |     |     | 330 |     |     |     | 335 |     |
|-----|-----|-----|-----|-----|-----|-----|-----|-----|-----|-----|-----|-----|-----|-----|-----|-----|-----|
| Ser | Glu | Gly | Thr | Asn | Ser | Thr | Leu | Thr | Leu | Ser | Pro | Val | Ser | Phe | Glu |
|     |     |     | 340 |     |     |     |     | 345 |     |     |     | 350 |     |     |     |
| Asn | Glu | His | Ser | Tyr | Leu | Cys | Thr | Val | Thr | Cys | Gly | His | Lys | Lys | Leu |
|     |     |     | 355 |     |     |     |     | 360 |     |     |     | 365 |     |     |     |
| Glu | Lys | Gly | Ile | Gln | Val | Glu | Leu | Tyr | Thr | Phe | Pro | Arg | Asp | Pro | Glu |
|     |     | 370 |     |     |     |     | 375 |     |     |     | 380 |     |     |     |     |
| Ile | Glu | Met | Ser | Gly | Gly | Leu | Val | Asn | Gly | Ser | Ser | Val | Thr | Val | Ser |
| 385 |     |     |     |     | 390 |     |     |     |     | 395 |     |     |     |     | 400 |
| Cys | Lys | Val | Pro | Ser | Val | Tyr | Pro | Leu | Asp | Arg | Leu | Glu | Ile | Glu | Leu |
|     |     |     |     | 405 |     |     |     |     | 410 |     |     |     |     | 415 |     |
| Leu | Lys | Gly | Glu | Thr | Ile | Leu | Glu | Asn | Ile | Glu | Phe | Leu | Glu | Asp | Thr |
|     |     |     |     | 420 |     |     |     |     | 425 |     |     |     |     | 430 |     |
| Asp | Met | Lys | Ser | Leu | Glu | Asn | Lys | Ser | Leu | Glu | Met | Thr | Phe | Ile | Pro |
|     |     | 435 |     |     |     |     | 440 |     |     |     |     | 445 |     |     |     |
| Thr | Ile | Glu | Asp | Thr | Gly | Lys | Ala | Leu | Val | Cys | Gln | Ala | Lys | Leu | His |
|     | 450 |     |     |     |     | 455 |     |     |     |     | 460 |     |     |     |     |
| Ile | Asp | Asp | Met | Glu | Phe | Glu | Pro | Lys | Gln | Arg | Gln | Ser | Thr | Gln | Thr |
| 465 |     |     |     |     | 470 |     |     |     |     | 475 |     |     |     |     | 480 |
| Leu | Tyr | Val | Asn | Val | Ala | Pro | Arg | Asp | Thr | Thr | Val | Leu | Val | Ser | Pro |
|     |     |     |     | 485 |     |     |     |     | 490 |     |     |     |     | 495 |     |
| Ser | Ser | Ile | Leu | Glu | Glu | Gly | Ser | Ser | Val | Asn | Met | Thr | Cys | Leu | Ser |
|     |     |     | 500 |     |     |     |     | 505 |     |     |     | 510 |     |     |     |
| Gln | Gly | Phe | Pro | Ala | Pro | Lys | Ile | Leu | Trp | Ser | Arg | Gln | Leu | Pro | Asn |
|     |     | 515 |     |     |     |     | 520 |     |     |     |     | 525 |     |     |     |
| Gly | Glu | Leu | Gln | Pro | Leu | Ser | Glu | Asn | Ala | Thr | Leu | Thr | Leu | Ile | Ser |
|     | 530 |     |     |     |     | 535 |     |     |     |     |     | 540 |     |     |     |
| Thr | Lys | Met | Glu | Asp | Ser | Gly | Val | Tyr | Leu | Cys | Glu | Gly | Ile | Asn | Gln |
| 545 |     |     |     |     | 550 |     |     |     |     | 555 |     |     |     |     | 560 |
| Ala | Gly | Arg | Ser | Arg | Lys | Glu | Val | Glu | Leu | Ile | Ile | Gln | Val | Thr | Pro |
|     |     |     |     | 565 |     |     |     |     | 570 |     |     |     |     | 575 |     |
| Lys | Asp | Ile | Lys | Leu | Thr | Ala | Phe | Pro | Ser | Glu | Ser | Val | Lys | Glu | Gly |
|     |     |     | 580 |     |     |     |     | 585 |     |     |     | 590 |     |     |     |
| Asp | Thr | Val | Ile | Ile | Ser | Cys | Thr | Cys | Gly | Asn | Val | Pro | Glu | Thr | Trp |
|     |     | 595 |     |     |     |     | 600 |     |     |     |     | 605 |     |     |     |
| Ile | Ile | Leu | Lys | Lys | Lys | Ala | Glu | Thr | Gly | Asp | Thr | Val | Leu | Lys | Ser |
|     | 610 |     |     |     |     | 615 |     |     |     |     | 620 |     |     |     |     |
| Ile | Asp | Gly | Ala | Tyr | Thr | Ile | Arg | Lys | Ala | Gln | Leu | Lys | Asp | Ala | Gly |
| 625 |     |     |     |     | 630 |     |     |     |     | 635 |     |     |     |     | 640 |
| Val | Tyr | Glu | Cys | Glu | Ser | Lys | Asn | Lys | Val | Gly | Ser | Gln | Leu | Arg | Ser |
|     |     |     |     | 645 |     |     |     |     | 650 |     |     |     |     | 655 |     |
| Leu | Thr | Leu | Asp | Val | Gln |
|     |     |     | 660 |     |     |

( 2 ) INFORMATION FOR SEQ ID NO:8:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: nucleic acid ( x i ) SEQUENCE DESCRIPTION: SEQ ID NO:8:

AATTTATGTG TGTGAAGGAG        20

( 2 ) INFORMATION FOR SEQ ID NO:9:

( i ) SEQUENCE CHARACTERISTICS:
       ( A ) LENGTH: 17 bases
       ( B ) TYPE: nucleic acid
       ( C ) STRANDEDNESS: single
       ( D ) TOPOLOGY: linear ( i i ) MOLECULE TYPE: nucleic acid ( x i ) SEQUENCE DESCRIPTION: SEQ ID NO:9:

TTCTGTGAAT ATGACAT    17

( 2 ) INFORMATION FOR SEQ ID NO:10:

( i ) SEQUENCE CHARACTERISTICS:
       ( A ) LENGTH: 32 bases
       ( B ) TYPE: nucleic acid
       ( C ) STRANDEDNESS: single
       ( D ) TOPOLOGY: linear ( i i ) MOLECULE TYPE: nucleic acid ( x i ) SEQUENCE DESCRIPTION: SEQ ID NO:10:

GGGTCATATA GTCTTGTAGA AGCACAGAAA TC    32

( 2 ) INFORMATION FOR SEQ ID NO:11:

( i ) SEQUENCE CHARACTERISTICS:
       ( A ) LENGTH: 32 bases
       ( B ) TYPE: nucleic acid
       ( C ) STRANDEDNESS: single
       ( D ) TOPOLOGY: linear ( i i ) MOLECULE TYPE: nucleic acid ( x i ) SEQUENCE DESCRIPTION: SEQ ID NO:11:

GAGCTGAATA CCCTCCCAGG CACACACAGG TG    32

( 2 ) INFORMATION FOR SEQ ID NO:12:

( i ) SEQUENCE CHARACTERISTICS:
       ( A ) LENGTH: 27 bases
       ( B ) TYPE: nucleic acid
       ( C ) STRANDEDNESS: single
       ( D ) TOPOLOGY: linear ( i i ) MOLECULE TYPE: nucleic acid ( x i ) SEQUENCE DESCRIPTION: SEQ ID NO:12:

GGGTTTTGGA ACCACTATTT TGTCATC    27

( 2 ) INFORMATION FOR SEQ ID NO:13:

( i ) SEQUENCE CHARACTERISTICS:
       ( A ) LENGTH: 35 bases
       ( B ) TYPE: nucleic acid
       ( C ) STRANDEDNESS: single
       ( D ) TOPOLOGY: linear ( i i ) MOLECULE TYPE: nucleic acid ( x i ) SEQUENCE DESCRIPTION: SEQ ID NO:13:

GTTAACACT TGATGTTCAA GGAAGAGAAA ACTAA    35

MONONUCLEAR LEUKOCYTE DIRECTED ENDOTHELIAL ADHESION MOLECULE ASSOCIATED WITH ATHEROSCLEROSIS

CROSS REFERENCE TO RELATED APPLICATION

This Application is a continuation of application Ser. No. 07/649,565, filed Feb. 1, 1991, now abandoned which is a Continuation-In-Part of U.S. application Ser. No. 07/487,038, filed Mar. 2, 1990, now abandoned.

STATEMENT AS TO RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

FIELD OF THE INVENTION

This invention relates to endothelial cell proteins involved in mononuclear leukocyte adherence to endothelial cells and their role in the development of atherosclerotic lesions in mammals.

BACKGROUND OF THE INVENTION

The endothelial lining of blood vessels normally plays a critical role in maintaining homeostasis at the vessel wall-blood interface (Gimbrone, M. A., Jr., in *Vascular Endothelium in Hemostasis and Thrombosis*, Ed. Churchill Livingston, Edinburgh, p. 1 (1986); Gryglewski, R. J. et al., *Hypertension* 12:530 (1988)). However, changes to the endothelial lining have been implicated in development of atherosclerotic lesions. Ultrastructural and immunohistochemical studies in various animal models and human tissues have established that the adherence of blood monocytes to endothelial cells (EC) lining large arteries is one of the earliest detectable events in atherosclerosis (Gerrity, R. G. et al., *Am. J. Pathol.* 95:775 (1979); Gerrity, R. G., *Am. J. Pathol.* 103:181 (1981); Gerrity, R. G., *Am. J. Pathol.* 103:191 (1981); Joris, I. et al., *Am. J. Pathol.* 113:341 (1983); Klurfeld, D. M., *Arch. Pathol. Lab. Med.* 109:445 (1985); Schaffner, T. et al., *Am. J. Pathol.* 100:57 (1980); Gown, A. M. et al., *Am. J. Pathol.* 125:191 (1986); Faggiotto, A. et al., *Arteriosclerosis* 4:323 (1984); Faggiotto, A. et al., *Arteriosclerosis* 4:341 (1984); Fowler, S. et al., *Lab. Invest.* 41:372 (1979); Watanabe, T. et al., *Lab Invest.* 53:80 (1985); Walker, L. N. et al., *Am. J. Pathol.* 125:450 (1986); Schwartz, C. J. et al., *Virchows Arch. (Path. Anat.)* 405:175 (1985); Lewis, C. J. et al., *Ann. NY Acad. Sci.* 454:91 (1985)). The subsequent transendothelial migration of monocytes, their accumulation in the intima and development into lipid-engorged "foam cells", appear to be important steps in the initiation of atherosclerotic lesions (Ross, R., *N. Eng. J. Med.* 314:488 (1986); Davies, P. F., *Lab. Invest.* 55:5 (1986); Munro, J. M. et al., *Lab. Invest.* 58:249 (1988)).

Monocytes and macrophage foam cells may also contribute to the progression of atherosclerotic lesions by producing cytokines and growth factors (Libby, P., *Molecular Aspects of Medicine* 96:499 (1987)). These in turn may amplify recruitment, induce migration of smooth muscle cells into the intima (Ross, R., *N. Eng. J. Med.* 314:488 (1986)), stimulate cell replication (Libby, P. et al., *New Eng. J. Med.* 318:1493 (1988)), and modify the immunologic state of lesions through lymphocyte recruitment and induction of Class II MHC antigens (Hansson, G. K. et al., *Arteriosclerosis* 9:567 (1989)).

The initial step in leukocyte migration, whether in atherosclerosis or in inflammation, is the adherence of a circulating leukocyte to the endothelial lining. In atherosclerosis, the migration of monocytes into the arterial intima and the resulting formation or expansion of atherosclerotic lesions, is a localized phenomenon (Gerrity, R. G. et al., *Am. J. Pathol.* 95:775 (1979); Gerrity, R. G., *Am. J. Pathol.* 103:181 (1981); Gerrity, R. G., *Am. J. Pathol.* 103:191 (1981); Joris, I. et al., *Am. J. Pathol.* 113:341 (1983); Klurfeld, D. M., *Arch. Pathol. Lab. Med.* 109:445 (1985); Schaffner, T. et al., *Am. J. Pathol.* 100:57 (1980); Gown, A. M. et al., *Am. J. Pathol.* 125:191 (1986); Faggiotto, A. et al., *Arteriosclerosis* 4:323 (1984); Faggiotto, A. et al., *Arteriosclerosis* 4:341 (1984); Fowler, S. et al., *Lab. Invest.* 41:372 (1979); Watanabe, T. et al., *Lab Invest.* 53:80 (1985); Walker, L. N. et al., *Am. J. Pathol.* 125:450 (1986); Schwartz, C. J. et al., *Virchows Arch. (Path. Anat.)* 405:175 (1985); Lewis, C. J. et al., *Ann. NY Acad. Sci.* 454:91 (1985); Ross, R., *N. Eng. J. Med.* 314:488 (1986); Davies, P. F., *Lab. Invest.* 55:5 (1986); Munro, J. M. et al., *Lab. Invest.* 58:249 (1988)), and, therefore, local mechanisms presumably are operative. On the other hand, systemic factors such as hypercholesterolemia may contribute indirectly to atherosclerotic lesion localization.

In swine, hypercholesterolemia induces the production of a subpopulation of monocytes in the bone marrow, which unlike monocytes from normocholesterolemic animals respond to a monocyte-selective chemoattractant (Averill, L. E., *Am. J. Pathol.* 135:369 (1989); Gerrity, R. G., et al., in *Vascular Dynamics*, Westerhof, N., et al. (eds.), Plenum Press, p. 237 (1989)). Such a chemoattractant has been found in areas of the pig aorta that are prone to develop foam cell lesions (Gerrity, R. G., et al., *Arteriosclerosis* 5:55 (1985)). In addition, the monocytosis seen in these animals may facilitate monocyte recruitment.

Endothelial hyperadhesive surface change may occur through protein synthesis-dependent or -independent mechanisms. In acute inflammation, both mechanisms appear to be operative (Cybulsky, M. I., et al., *Am. J. Pathol.* 135:227 (1989)). Protein synthesis-dependent mechanisms involve the expression of endothelial-leukocyte adhesion molecules (ELAMs) (Cotran, R. S., et al., *J. Exp. Med.* 164:661 (1986); Munro, J. M., et al., *Am. J. Pathol.* 135:121 (1989)), and signify endothelial activation (Cotran, R. S., et al., in *Endothelial Cell Biology*, Simionescu, N., et al. (eds.), Plenum Publishing, New York, p. 335 (1988)). Several such endothelial surface structures have been identified, including endothelial leukocyte adhesion molecule-1 (ELAM-1) (Bevilacqua, M. P., et al., *Proc. Natl. Acad. Sci. USA*: 84:9238 (1987); Bevilacqua, M. P., et al., *Science* 243:1160 (1989)), ICAM-1 (Smith, C. W., et al., *J. Clin. Invest.* 83:2008 (1989); Simmons, D., et al., *Nature* 331:624 (1988); Staunton, D. E., et al., *Cell* 52:925 (1988)), ICAM-2 (Staunton, D. E., et al., *Nature* 339:61 (1989)), INCAM-110 (Rice, G. E., et al., *Science* 246:1303 (1989)), and VCAM-1 (Osborn, L., et al., *Cell* 59:1203 (1989)). In cultured EC and in inflammatory reactions, their expression is upregulated by bacterial endotoxin (lipopolysaccharide, LPS) and inflammatory cytokines (interleukin-1, IL-1, and tumor necrosis factor, TNF).

Certain of these EC adhesion molecules exhibit leukocyte selectivity, e.g., ELAM-1 appears to primarily support the adhesion of neutrophils, not lymphocytes or lymphoid cell lines. ICAM-1, through its interaction with CD11a/CD18, may be involved in various EC-leukocyte interactions (Springer, T. A., *Nature* 346:425–434 (1990)). In contrast to ELAM-1 and ICAM-1, VCAM-1, also identified as INCAM-110 (Rice, G. E. et al., *J. Exp. Med.* 171:1369 (1990)), is a leukocyte adhesion molecule that supports the adhesion of human monocytes, lymphocytes, myelomonocytic and lymphocytic leukocyte cell lines, but not of peripheral blood neutrophils (Osborn, L. et al., *Cell* 59:1203 (1989), Rice, G. E. et al., *J. Exp. Med.* 171:1369 (1990)).

The patterns of ELAM distribution has been examined predominantly in normal tissues and in inflammatory conditions. ELAM-1 is not expressed by normal adult tissues and, in inflammation, is induced only in endothelium of post-capillary venules and small veins (Cotran, R. S. et al., *J. Exp. Med.* 164:661–666 (1989); Cotran, R. S. et al., *J. Immunol.* 140:1883–1886 (1988); Munro, J. M. et al., *Am. J. Pathol.* 135:121–133 (1989)). ICAM-1 is expressed constitutively in endothelium and other cell types (Dustin, M. L. et al., *J. Immunol.* 137:245–254 (1986)), but can be upregulated in various pathophysiologic settings. In inflammatory reactions, enhanced endothelial expression of ICAM-1 is limited predominantly to postcapillary venules and small veins (Cotran, R. S. et al., *J. Immunol.* 140:1883–1886 (1988); Munro, J. M. et al., *Am. J. Pathol.* 135:121–133 (1989)); however, it also has been detected in endothelium of normal arterioles (Faull, R. J. and Russ G. R., *Transplant* 48:226–230 (1989)).

None of the previously described ELAMs have been demonstrated in atherosclerotic lesions or implicated in the development and/or progression of such lesions.

SUMMARY OF THE INVENTION

The invention relates to protein molecules, designated ATHERO-ELAMs, expressed by endothelial cells. ATHERO-ELAMs are selective for mononuclear leukocytes, are involved in monocyte and lymphocyte adhesion to endothelial cells, and are markers for early atherosclerotic lesions in blood vessels. The invention also relates to monoclonal antibodies specific for an ATHERO-ELAM and uses of these monoclonal antibodies in diagnosis of atherosclerosis and in intervention during its progression. The invention further relates to the use of soluble forms of ATHERO-ELAMs to intervene with the progression of atherosclerosis.

DESCRIPTION OF THE FIGURES

FIG. 1A is a graph which plots the level of adhesion of U937 cells to aortic endothelial cells (Ao EC) and inferior vena cava cells (IVC EC). Adhesion is measured as a function of time after activation of endothelial cells with *E. coli* LPS (1 µg/ml).

FIG. 1B is a bar graph which shows the effect of cyclohexamide (CHX, 10 µg/ml) on adhesion of U937 cells to IVC EC at 0 hours and 5 hours after activation of the IVC EC with LPS.

FIG. 1C is a graph which plots the binding of monoclonal antibodies (MAb) Rb2/3 and Rb1/9 to Ao EC and of monoclonal antibody Rb1/9 to IVC EC. MAb binding is measured as a function of time after activation of endothelial cells with *E. coli* LPS (1 µg/ml).

FIG. 1D is a bar graph which shows the effect of cyclohexamide on the binding of MAb Rb1/9 to IVC EC at 0 hours and 5 hours after activation of the IVC EC with LPS. The inset in FIG. 1D shows that CHX did not affect the binding of MAb Rb2/3 to an EC antigen, the expression of which was not altered by LPS.

The bar graph on the right shows the effect of MAb Rb 1/9, Rb2/4 and Rb2/3 pretreatment on adhesion of U937 cells to venous EC at 0, 5 hours and 24 hours after activation of the EC cells by LPS.

Figure 2:
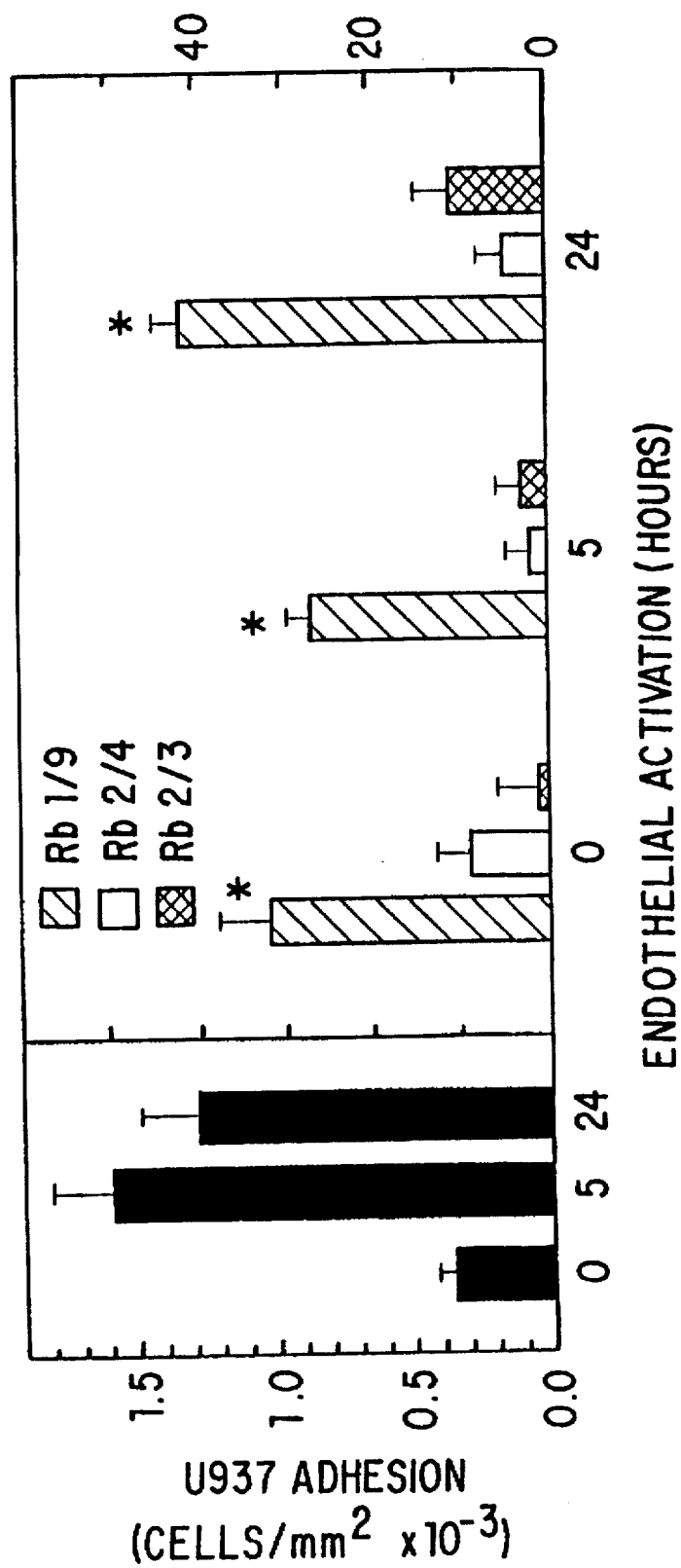
FIG. 2 consists of two bar graphs. The bar graph on the left shows the adhesion of U937 cells to venous EC at 5 and 24 hours after activation by LPS.
Figure 3:
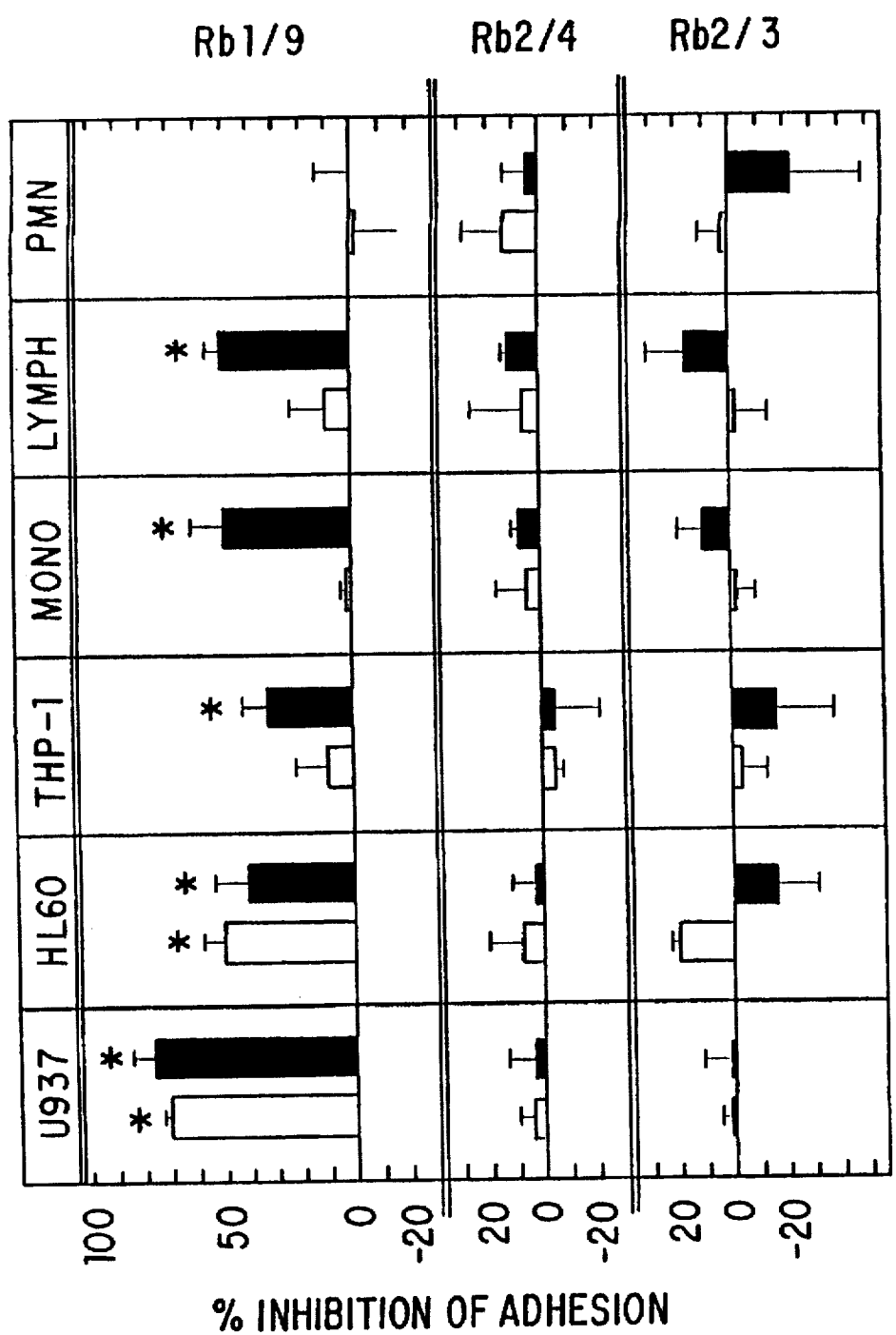
Figure 4A:
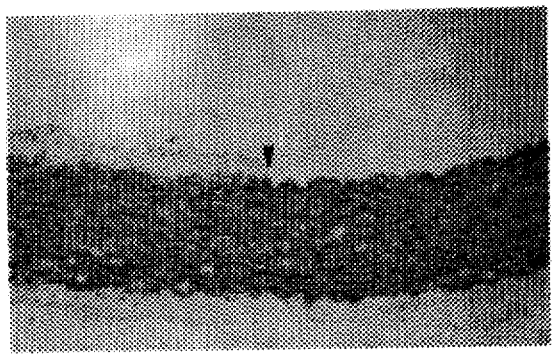
Figure 4B:
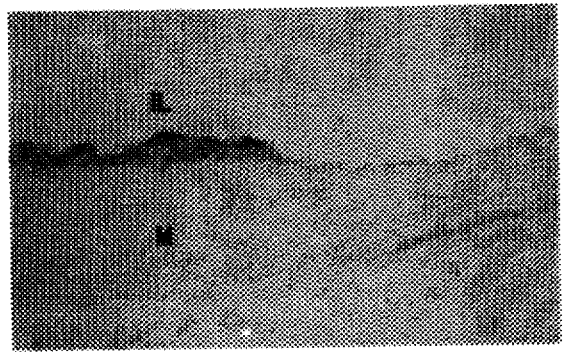
Figures 4C, 4D:
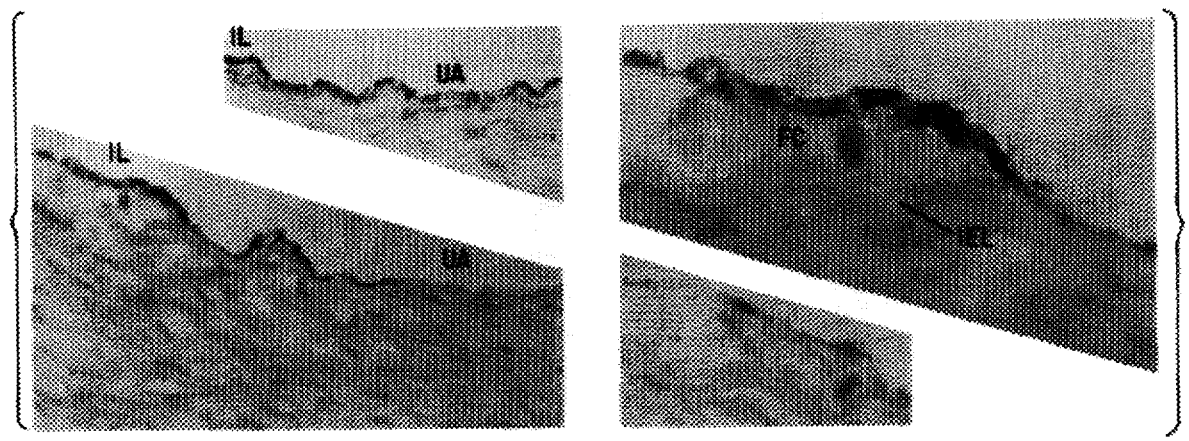
Figure 4E:
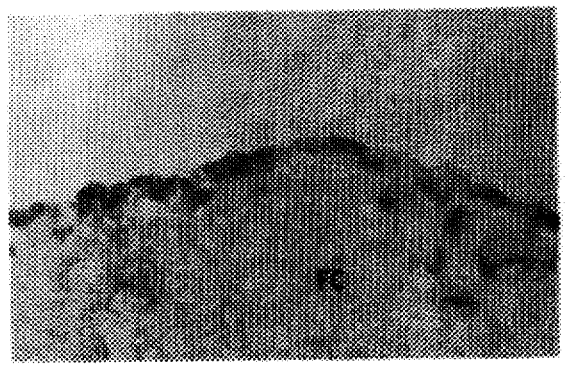
Figure 4F:
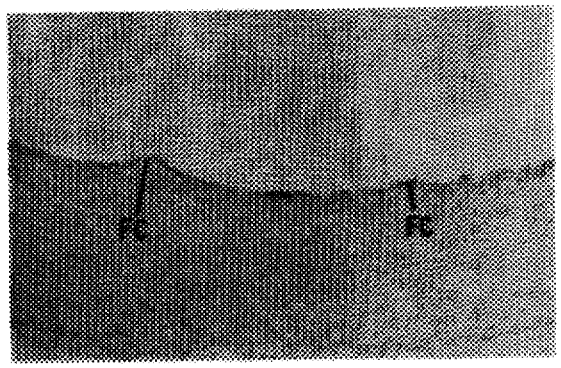

FIG. 3 is a bar graph illustrating the inhibition of leukocyte adhesion with F(ab')$_2$ fragments to 18 h LPS-treated rabbit aortic endothelium. At 4° C. (open bars), Rb1/9 F(ab')$_2$ significantly inhibited the adhesion of U937, HL60 and THP-1 cell lines, as well as human blood monocytes and lymphocytes (upper panel). U937 and HL60 adhesion was also inhibited in assays performed at 37° C. (solid bars). Significant decreases in adhesion were not observed with Rb2/4 or Rb2/3 F(ab')$_2$ (middle and lower panels).

FIG. 4 is a photograph illustrating immunohistochemical staining of rabbit aortas. (A–D) Frozen sections of the same atherosclerotic lesion located in the descending thoracic aorta from a rabbit fed a 1% cholesterol diet for 9 weeks (arrowhead marks edge of lesion). (A) Stained for smooth muscle cells with MAb CGA7. (B) Stained for rabbit macrophages with MAb RAM 11. (C,D) Stained for ATHERO-ELAM with Rb1/9. (C inset, goat anti-human von Willebrand Factor, 1/3000 dil. of IgG, Atlantic Ab., bar=50 µm). (D inset, culture supernatant, bar=10 µm). (E) Rb1/9 staining of EC overlying an intimal foam cell-rich lesion in the aortic arch of an 18-week WHHL rabbit (bar=10 µm). (F) Focal ATHERO-ELAM expression associated with small foam cell aggregates in the descending thoracic aorta of a rabbit with dietary hypercholesterolemia (bar=100 µm).

FIG. 5 A and B illustrate autoradiograms of reduced SDS-polyacrylamide gels, demonstrating specific indirect immunoprecipitation of polypeptides with MAb Rb1/9.

FIG. 6 illustrates the homology between the N-terminal amino acid sequence of purified 98K ATHERO-ELAM (Sequence ID 2, amino acids 1–22) and the predicted N-terminal sequence of human VCAM-1 (Sequence ID 7, amino acids 1–22).

FIG. 7 illustrates the nucleotide sequence of rabbit ATHERO-ELAM (Sequence ID 1). The underlined region in the Figure indicates a newly identified alternatively spliced region designated AS-III. Rabbit ATHERO-ELAM was cloned using an oligonucleotide probe based on the N-terminal amino acid sequence (FIG. 6) from a lambda gt11 cDNA library constructed with mRNA from LPS-stimulated (4 hr) rabbit venous endothelium.

FIG. 8 illustrates the deduced amino acid sequence of rabbit ATHERO-ELAM (Sequence ID 2).

FIG. 9 illustrates and compares the nucleotide sequences of rabbit ATHERO-ELAM (Sequence ID 6) and human VCAM-1 (Sequence ID 3) AS-I domains.

Figure 10A:
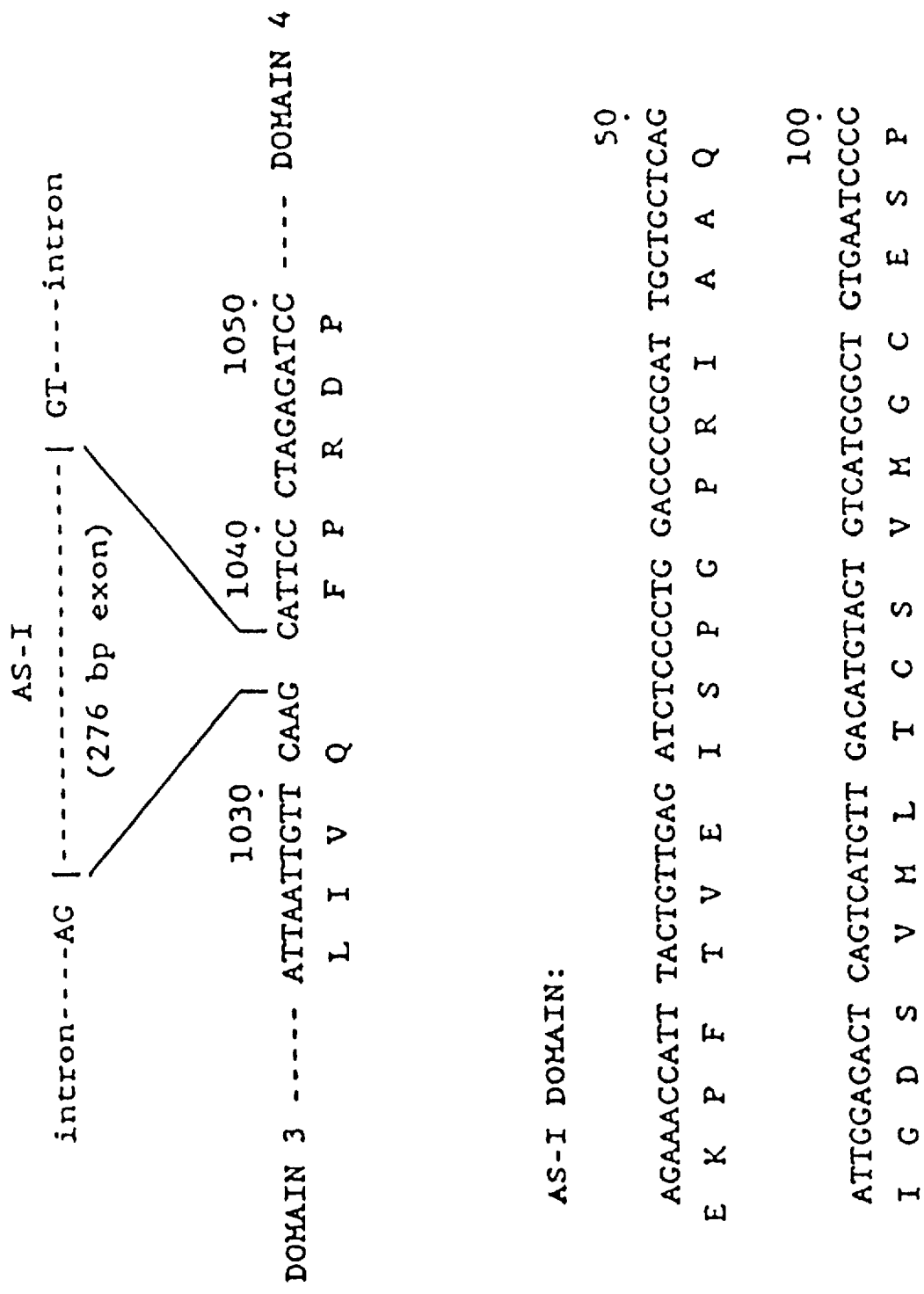

FIG. 10 illustrates the nucleotide sequence, deduced amino acid sequence, and location of an alternatively spliced human exon designated AS-I (Sequence ID 3 and 5) with respect to human VCAM-1 cDNA. The potential N-linked glycosylation site is underlined.

FIG. 11 illustrates the extracellular structure of the 7 immunoglobulin-like domain form of human VCAM-1 (Sequence ID 7). The sequence was aligned to residues conserved in C2 or H type immunoglobulin regions (Hunkapiller, T., et al., *Adv. in Immunol.* 44:1–63 (1989)). Cysteine residues forming disulfide bridges in each domain are indicated with arrowheads.

Figure 12:
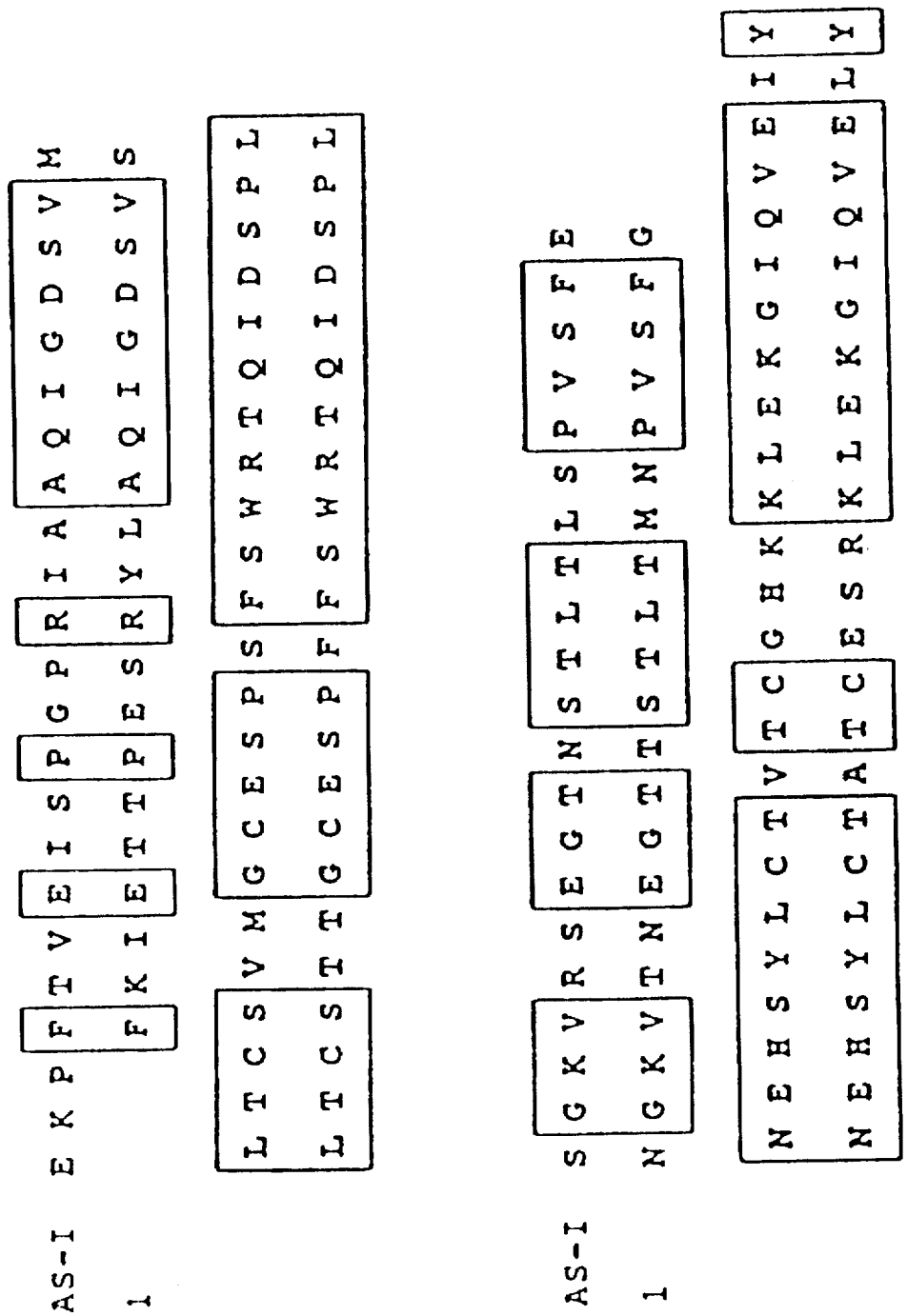

FIG. 12 illustrates the structural homology between human AS-I (Sequence ID 5) and domain 1 (Sequence ID 7, amino acids 1–89). Sequences were aligned by inspection, and homologous regions boxed (AS-I, top; domain 1, bottom).

Figure 13A:
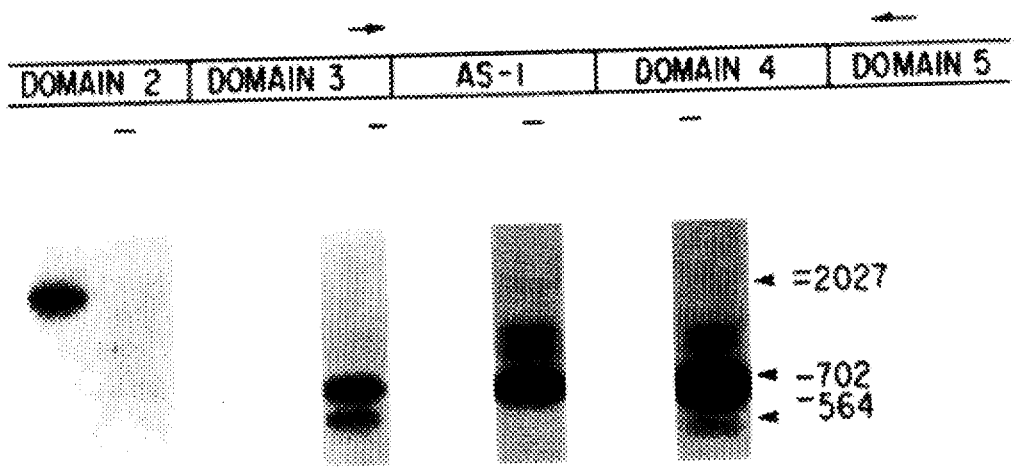

FIG. 13A illustrates the identification of 7 and 6 immunoglobulin-like domain forms of VCAM-1 in IL-1-activated human umbilical endothelium. PCR was performed with primers corresponding to regions of domains 3 and 5 as indicated by the upper arrows. These primers should generate 740 and 464 bp products from VCAM-1 cDNA with and without the AS-I domain respectively. Southern blotting using oligonucleotide probes corresponding to the underlined regions of domains 3, AS-I, and 4 confirmed the presence of both species. As expected, the domain 3 and 4 probes hybridized to both 740 and 464 bp species, whereas the AS-I probe only to the 740 bp product. A domain 2 probe, which was 5' of the region amplified by PCR, did not hybridize with either product (right lane). All the above probes hybridized to a 2.05 kb PCR product generated with primers spanning the 7 extracellular immunoglobulin-like domains of VCAM-1 (results with domain 2 probe shown, left lane). Relevant hybridization is indicated by arrowheads. Molecular weight standards are bacteriophage lambda DNA digested with Hind III and Bst E II (right).

Figure 13B:
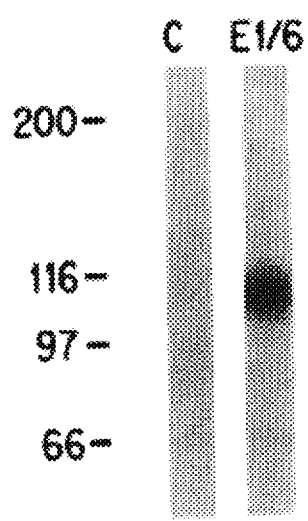

FIG. 13B is a photograph of an autoradiogram of a reduced SDS polyacrylamide gel demonstrating immunoprecipitation of a 110 kD polypeptide from surface-iodinated, TNF-treated (24h) human umbilical vein endothelial cells with MAb E1/6 (C is a control, nonbinding MAb). Identical results were obtained with MAb Hu8/4, which like E1/6 is directed to human VCAM-1.

FIG. 14 illustrates the amino acid sequences of human VCAM-1 (Sequence ID 7) and rabbit ATHERO-ELAM (Sequence ID 2). The sequences were aligned as in FIG. 11. SP=Signal Peptide; TM/Cyto: Transmembrane and cytoplasmic region; the transmembrane region is underlined. A human AS-III exon region corresponding to the rabbit AS-III exon has been identified.

DETAILED DESCRIPTION OF THE INVENTION

The present invention relates to a novel ELAM, designated ATHERO-ELAM.

By "ATHERO-ELAM" is meant an endothelial cell surface protein expressed at sites of ongoing/active atherosclerosis which participates in leukocyte-endothelial adhesion.

By "VCAM-1" is meant a member of the immunoglobulin gene superfamily, which is induced on the surface of endothelial cells by certain cytokines.

By "in substantially pure form" in reference to a protein is meant that the protein is free of other components of biological origin.

By "binding characteristics" in reference to an antibody is meant a molecule capable of recognizing and binding to the protein or fragment thereof for which the antibody is specific.

By "monocyte-binding equivalent" or "mononuclear leukocyte-binding equivalent" in reference to a protein or polypeptide is meant a second protein or fragment thereof which is also capable of binding to a monocyte or mononuclear leukocyte, despite differing from the protein or polypeptide by one or more amino acids.

By "water-soluble part of ATHERO-ELAM" is meant the extracellular part of ATHERO-ELAM. According to the invention, the water-soluble part contains amino acids 1–774 of Sequence ID 2.

Induction and Assays of ATHERO-ELAM

ATHERO-ELAM can be induced in endothelial cells by bacterial endotoxin, lipopolysaccharide (LPS). In culture, the inducible endothelial cell surface protein supports adhesion of monocyte-like U937 cells. U937 adhesion becomes increased over basal levels after 1–2 hours of LPS treatment, reaches a maximum at 6–8 hours, and remains sustained through 96 hours. Inhibition of protein synthesis with cycloheximide prevents this adhesive change.

Initially, an in vitro system was developed to facilitate the study of monocyte-endothelial adhesive interactions. EC cultures were established from large vessels (aorta and inferior vena cava) of normal New Zealand White rabbits. From everted vessels, EC were isolated with 0.2% or 0.4% collagenase respectively, and cultured on gelatin-coated tissue culture plastic in Medium 199 (Hank's salts) containing 20% fetal bovine serum (FBS), 10–20 µg/ml EC mitogen (Biomedical Technologies, Inc.), and 20–40 µg/ml porcine intestinal heparin (Sigma, grade I) (Cybulsky, M. I. et al., *FASEB J.* 2:A1603 (1988); Danthuluri, N. R. et al., *Am. J. Physiol.* 255 (Heart Circ. Physiol. 24):H1549–H1553 (1988) ). These cells grew to form confluent monolayers that exhibited features characteristic of differentiated endothelium. Activation of rabbit EC with Gram negative bacterial endotoxin (lipopoly-saccharide, LPS) resulted in a hyperadhesive surface change that was demonstrable with rabbit leukocytes (Cybulsky, M. I. et al., *FASEB J.* 3:A1319 (1989)) and human blood monocytes (Territo, M. C. et al., *Arteriosclerosis* 9:824 (1989); Berliner, J. A. et al., *J. Clin. Invest.* 85:1260 (1990)).

The U937 cell, a human leukocyte cell line with adhesive properties similar to monocytes (DiCorleto, P. E. et al., *J. Clin. Invest.* 75:1153 (1985)) was selected to further characterize this adhesive change. The human promyelocytic HL60 cell line was used for comparison. U937 adhesion to rabbit aortic and venous EC became increased over basal levels after 1–2 h of LPS treatment, reached maximum at 6–8 h and remained sustained through 96 h. Inhibition of protein synthesis with cycloheximide abrogated this adhesive change. Similar results were obtained with HL60 cells.

Monoclonal Antibodies to ATHERO-ELAM

In order to identify ELAMs mediating the increase in U937 adhesion, monoclonal antibodies (MAb's) to inducible EC surface antigens were produced. From a panel of MAb's generated to LPS-activated EC, three MAb's, designated Rb1/9, Rb2/3 and Rb2/4 (all IgG$_1$ immunoglobulins), were selected for their ability to recognize LPS-inducible EC surface antigens in a cell surface fluorescence immunoassay. The time course of binding of MAb Rb1/9 was similar to the EC adhesive change for U937 cells (low in untreated EC, reaching maximum in 6–8 h and sustained through 96 h), and cycloheximide treatment ablated Rb1/9 antigen surface expression both in basal and activated monolayers. The binding profile of MAb Rb2/4 was virtually identical to that of Rb1/9, whereas MAb Rb2/3 recognized a surface epitope with higher basal expression and a sustained LPS-induced elevation.

The functional role of these inducible EC surface antigens in supporting U937 adhesion was then assessed in adhesion blocking assays. Pretreatment with saturating concentrations of Rb1/9 significantly inhibited U937 adhesion to basal and 5 h- or 24 h-activated EC monolayers. In contrast, a decreased adhesion was not observed with other MAb's of the same immunoglobulin class, including Rb2/4 which appears to recognize the same molecule as Rb1/9, and Rb2/3 which bound to basal and activated EC surfaces at higher densities than Rb1/9. MAb Rb2/13, which recognized a constitutive antigen expressed at high levels on control and LPS-treated rabbit EC, also did not inhibit U937 adhesion. None of the MAb's inhibited HL60 cell adhesion. These results demonstrate the specificity of Rb1/9 in blocking adhesion of monocyte-like U937 cells, and implicate the Rb1/9-binding epitope as important to adhesion of mononuclear leukocytes.

Having identified an inducible EC surface protein which appeared to support mononuclear cell adhesion in vitro, an immunohistochemical technique was used to examine its expression in atherogenesis. In rabbits fed a 1% hypercholesterolemic diet and in Watanabe heritable hyperlipidemic (WHHL) rabbits, specific staining with Rb1/9 was localized to aortic endothelium covering foam cell-rich intimal lesions at various stages of their development. Of particular interest was staining of EC extending beyond the edges of intimal lesions, and locally in regions with very small intimal accumulations of foam cells. Aortic EC in uninvolved regions of these hypercholesterolemic animals, as well as EC in large arteries and veins of normal rabbits, were uniformly unstained. This selective pattern of immunohistochemical staining establishes the inducible ELAM recognized by Rb1/9 as an ATHERO-ELAM.

The biochemical nature of Rb1/9 antigen was determined by immunochemical studies and amino acid sequencing. From total cell lysates of biosynthetically labeled LPS-activated EC monolayers, Rb1/9 specifically immunoprecipitated two polypeptides, with relative molecular weights of 118K and 98K on reduced SDS-PAGE. Both polypeptides appeared to be expressed on the EC surface, as determined by immunoprecipitating cell lysates from surface iodinated monolayers. The relationship of the polypeptides was further investigated by Western blotting. The Rb1/9-binding epitope was found on both polypeptides, which suggests that they are not a heterodimeric complex. Together, these immunochemical data indicate that the inducible molecule recognized by MAb Rb1/9 is a newly synthesized protein, expressed on the EC surface in two forms. MAb Rb2/4 produced a similar immunoprecipitation pattern to Rb1/9, and cross-over immunoprecipitation established that both MAb recognized the same protein.

Structure of ATHERO-ELAM and Nucleotide Sequence Encoding ATHERO-ELAM

To elucidate the primary structure of the 2 polypeptides recognized by Rb1/9, they were purified from lungs of LPS-treated rabbits by immunoaffinity chromatography and SDS-PAGE, electrotransferred to Immobilon-P and N-terminal amino acid sequences obtained.

The 98K band showed high homology (20 of 22 amino acids, FIG. 6; Sequence ID 2, amino acids 1–22) to the predicted N-terminal sequence of human VCAM-1 (Sequence ID 7, amino acids 1–22), a recently cloned cytokine-inducible member of the immunoglobulin gene superfamily (Osborn, L., et al., Cell 59:1203–1211 (1989)). VCAM-1 has been identified on the surface of human EC and mediates the binding of mononuclear lymphocytes to EC. Expression of VCAM-1 by human EC was induced by the inflammatory cytokines interleukin-1 and tumor necrosis factor-alpha (Osborn et al.).

ATHERO-ELAM was cloned from a rabbit endothelial lambda gt11 cDNA library using an oligonucleotide probe based on the N-terminal amino acid sequence (FIG. 6; Sequence ID 1, amino acids 1–22). ATHERO-ELAM cDNA clones (the nucleotide sequences of the open reading frame are displayed in FIG. 7; Sequence ID 1) encoded two transmembrane proteins; one with 8, the other with 7 extracellular immunoglobulin-like domains (FIG. 14). These two proteins were identical, except for the presence of an additional extracellular immunoglobulin-like domain adjacent to the transmembrane domain. This domain, designated AS-III, is the result of alternative mRNA splicing.

The AS-III domain is encoded by 267 base pairs, having the sequence of nucleotides 2060–2326 in the rabbit ATHERO-ELAM open reading frame (FIG. 7, underlined sequence; Sequence ID 7, nucleotides 2060–2326). The presence of two forms of ATHERO-ELAM, which arise by alternative mRNA splicing, accounts for the two distinct polypeptides identified by immunoprecipitation with MAb Rb1/9 (FIG. 5), each sharing the same N-terminal amino acid sequences (FIG. 6). The AS-III domain was not identified in the published sequence of human VCAM-1 (Osborn, L., et al., Cell 59:1203–1211 (1989)).

Six of the rabbit ATHERO-ELAM extracellular immunoglobulin-like domains are highly homologous to the published sequence of human VCAM-1 (Osborn, L. et al., Cell 59:1203–1211 (1989); FIG. 14; Sequence ID 2). In addition to the AS-III domain, a second new immunoglobulin-like domain was identified. This domain, designated AS-I, is located between domains 3 and 4 (FIG. 14), is composed of 276 base pairs, and is encoded by nucleotides 929–1204 in FIG. 7 (Sequence ID 6). AS-I was present in all of the rabbit ATHERO-ELAM cDNA clones spanning this region (FIG. 14; Sequence ID 2).

Identification of the AS-I Domain in Human VCAM-1

In order to identify the AS-I domain in human VCAM-1 and to further compare ATHERO-ELAM and VCAM-1, a partial cDNA corresponding to the extracellular region of VCAM-1 was generated by PCR from IL-1-stimulated human umbilical vein endothelial cell (HUVEC) mRNA. This cDNA was 2.05 kb in length, and about 0.25 kb longer than would be predicted from the published human VCAM-1 sequence (Osborn et al.). Based on sequencing, the coding region of this amplified cDNA was identical to the previously reported VCAM-1 HUVEC cDNA clone (Osborn et al.) from amino acid residue 1 to 309 (Sequence ID 7), at which point the sequences diverge. At the nucleotide level, the sequences were identical to bp 1034 of the published sequence, and after an insertion of 276 bp (FIG. 10; Sequence ID 3), the two sequences resumed identity. The difference in the transcript structure lengthens the predicted protein by 92 residues between the third and fourth immunoglobulin domains.

The amino acid sequence of this additional region was homologous to the rabbit ATHERO-ELAM AS-I domain (FIG. 9). AS-I is an immunoglobulin-like domain of the C2 or H type, (Hunkapiller, T., et al., Adv. in Immunol. 44:1–63 (1989)), consistent with the other 6 extracellular domains of VCAM-1. Furthermore, this sequence was 73% homologous with the N-terminal immunoglobulin-like domain (domain 1) (FIG. 12; AS-I, Sequence ID 5; Domain 1, Sequence ID 7, amino acids 1–89). The AS-I domain also contains an additional potential N-linked glycosylation site.

To demonstrate that two VCAM-1 transcripts were derived by alternative mRNA splicing, the corresponding region of the human VCAM-1 gene was cloned from a human genomic library. A phage clone was obtained by screening a human genomic library with a rabbit partial cDNA. The AS-I domain corresponded to a single exon located between exons containing domains 3 and 4. Splice donor and acceptor sequences flanking the AS-I exon conform to consensus (Smith, C. W. J., et al., Ann. Rev. Genet. 23:527–577 (1989)). The nucleotide sequence of the AS-I exon was identical to that of the cDNA sequence obtained by PCR amplification. The 2.05 kb product generated by PCR amplification of VCAM-1 extracellular domains (FIG. 13A) suggested that a 7 domain form was the predominant mRNA species.

In order to confirm that IL-1-activated HUVEC express both forms of VCAM-1 mRNA, nested PCR was utilized. The same primers were used for first strand cDNA synthesis and first round PCR (see Example 15), however, nested primers were selected to regions in domains 3 and 5 (AATTTATGTGTGTGAAGGAG, Sequence ID 8 and TTCTGTGAATATGACAT, Sequence ID 9, respectively). By ethidium bromide staining and Southern blotting with oligonucleotide probes to regions of domain 3, AS-I and 4, the predominant PCR product was 740 bp (FIG. 13A), consistent with the 7 domain form. However, a 464 bp product which did not hybridize the AS-I probe was also identified, confirming that the 6 immunoglobulin domain form of VCAM-I was expressed by HUVEC.

The observation that the 7 domain VCAM-1 mRNA is predominant in activated HUVEC is consistent with expression of a 110 kD protein, determined by immunoprecipitation of biosynthetically labeled cells with monoclonal antibody E1/6 (Rice, G. E., et al., Science 246:1303–1306 (1989)). E1/6 blocked leukocyte adhesion to activated HUVEC (Rice, G. E., et al., Science 246:1303–1306 (1989); Rice, G. E., et. al., J. Exp. Med. 171:1369–1374 (1990)), and immunoprecipitation of surface iodinated HUVEC with MAbs E1/6 and Hu8/4 detected only the 110 kD polypeptide. (FIG. 13B).

Together, these data suggest that on the activated HUVEC surface, it is the 7 domain form which supports adhesion of mononuclear leukocytes. The 6 domain VCAM-1 cDNA expressed on transfected COS cells also supports mononuclear leukocyte adhesion (Osborn, L., et al., Cell 59:1203–1211 (1989); Elices, M. J., et al., Cell 60:577–584 (1990)). In light of the present demonstration of alternative splicing of the human VCAM-1 gene, it is possible that the 7 and 6 domain forms may have different affinities or subtle differences in specificities.

DESCRIPTION OF THE PREFERRED EMBODIMENTS

The DNA encoding ATHERO-ELAM can be utilized to produce genetic constructs which encode a soluble form of ATHERO-ELAM. Soluble transmembrane proteins can be produced by genetically engineering a cDNA containing a termination codon immediately 5' of the transmembrane domain. When expressed in appropriate cells, the protein synthesized from this cDNA is secreted and can be recovered from the culture medium.

The invention further relates to antibodies which recognize ATHERO-ELAM. Antibodies which recognize ATHERO-ELAM may be prepared by immunizing mice with cultured rabbit inferior vena cava (IVC) cells, which have been activated with LPS. Spleen cells from the immunized mice are fused with myeloma cells using methods known in the art (Kohler, G., et al., Nature 256:495 (1975); Goding, J. W., Monoclonal Antibodies: Principles and Practice, 2nd ed., Academic Press, London (1986)). Screening of the hybridomas with LPS-treated and control EC cells allows selection of monoclonal antibodies capable of binding to LPS-induced cell surface molecules. Further selection of monoclonal antibodies specific for ATHERO-ELAM is accomplished by determining the ability of the monoclonal antibodies to inhibit adhesion of monocyte-like U937 cells to control and activated EC cells.

Monoclonal antibody Rb1/9 is particularly effective in blocking U937 adhesion to activated EC monolayers. However, other monoclonal antibodies having the binding characteristics of the monoclonal antibodies described herein may also be utilized. The ability to block U937 adhesion to activated EC monolayers and the ability to bind to a newly synthesized protein, ATHERO-ELAM, on the activated EC surface, are binding characteristics of Rb1/9. The ability to bind to a newly synthesized protein, ATHERO-ELAM, on the activated EC surface, is a binding characteristic of Rb2/4.

Antibodies to ATHERO-ELAM may also be prepared by immunizing mice with recombinant ATHERO-ELAM, or ATHERO-ALAM fragments. By "ATHERO-ELAM" fragment is meant any polypeptide subset of the molecule. Particularly preferred ATHERO-ELAM fragments include monocyte-binding fragments. The monocyte-binding fragments may be obtained by cutting the ATHERO-ELAM cDNA with various restriction enzymes or exonucleases, cloning the resulting fragments, expressing these, and screening for monocyte binding activity according to methods known in the art.

The joining of various DNA fragments is performed in accordance with conventional procedures, employing blunt-ended or staggered-ended termini for ligation, restriction enzyme digestion to provide appropriate termini, filing in of cohesive ends as appropriate, alkali and phosphatase treatment to avoid undesirable joining, and ligation with appropriate ligases. The genetic construct may optionally encode a leader sequence to allow efficient expression of the recombinant protein.

To express the recombinant ATHERO-ELAM, transcriptional and translational signals recognized in an appropriate host element are necessary. Mammalian cells provide post-translational modification to recombinant protein molecules which provide for correct folding and glycosylation of appropriate sites. Mammalian cells which may be used in the practice of the invention include COS cells, Chinese hamster ovary (CHO) cells, leukocytes, myeloma cells or other transformed or oncogenic lymphocytes, e.g. EBV-transformed cells, cells of fibroblast origin such as VERO or cells of lymphoid origin, such as hybridoma SP2/O-AG-14 or the myeloma P3x63Sgh, and their derivatives. Other hosts include BHK cells and hepatoma cells.

In general, vectors containing replicon and control sequences which are derived from species compatible with a host cell are used in connection with the host. The vector ordinarily carries a replicon site, as well as specific genes which are capable of providing phenotypic selection in transformed cells. The expression of the gene encoding ATHERO-ELAM can also be placed under control with other regulatory sequences which may be homologous to the cell line in its untransformed state. For example, lactose-dependent E. coli chromosomal DNA comprises a lactose or lac operon which mediates lactose utilization by elaborating the enzyme beta-galactosidase. The lac control elements may be obtained from bacterial phage lambda plac5, which is infective for E. coli. The lac promoter-operator system can be induced by IPTG.

Other promoter/operator systems or portions thereof can be employed as well. For example, colicin E1, galactose, alkaline phosphatase, tryptophan, xylose, and the like can be used.

For mammalian hosts, several possible vector systems are available for expression. One class of vectors utilize DNA elements which are derived from animal viruses such as bovine papilloma virus, polyoma virus, adenovirus, vaccinia virus, baculovirus, retroviruses (RSV, MMTV or MOMLV), or SV40 virus. Cells which have stably integrated the DNA into their chromosomes may be selected by introducing one or more markers which allow selection of transfected host cells. The marker may provide for prototropy to an auxotrophic host, biocide resistance, e.g., antibiotics, or heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by Okayama, H., *Mol. Cel. Biol.*, 3:280 (1983) and others.

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After transfection, the cells are grown in media and screened for the appropriate activity using, for example, the above-described antibodies. Expression of the gene(s) results in production of the ATHERO-ELAM.

The transformed cells may be grown in appropriate nutrient medium in culture flasks or injected into a synergistic host, e.g., mouse or a rat, or immunodeficient host or host site, e.g., nude mouse or hamster pouch. In particular, the cells may be introduced into the abdominal cavity of an animal to allow production of ascites fluid which contains ATHERO-ELAM, or a fragment thereof. Alternatively, the cells may be injected subcutaneously and ATHERO-ELAM is harvested from the host. The cells may be used in the same manner as hybridoma cells.

The expressed ATHERO-ELAM, or fragment thereof, may be isolated from fermentation media or cell culture and purified in accordance with conventional conditions, such as extraction, precipitation, chromatography, affinity chromatography, electrophoresis or the like.

For example, ATHERO-ELAM may be purified by passing a solution containing the surface protein through a column containing an immobilized antibody which is specific for ATHERO-ELAM, for example, the above-described antibody Rb1/9. The desired protein may then be eluted by lowering the pH of the eluant.

It is also possible to use antibodies directed to ATHERO-ELAM to detect the presence of ATHERO-ELAM in tissue samples as an indication of expression of ATHERO-ELAM in association with disease processes. Thus, the invention also relates to a method of detecting endothelial cell expression of ATHERO-ELAM in a mammal by an assay for ATHERO-ELAM, comprising contacting a detectably labeled antibody directed to ATHERO-ELAM with a sample suspected of containing ATHERO-ELAM, or cell which expresses ATHERO-ELAM on its surface, and detecting whether a complex has formed.

The detection and quantitation of antigenic substances and biological samples frequently utilize immunoassay techniques. These techniques are based upon the formation of a complex between the antigenic substance being assayed, e.g., ATHERO-ELAM, and an antibody or antibodies in which one or the other member of the complex may be detectably labeled. In the present invention, the ATHERO-ELAM specific antibody may be labeled with any conventional label.

Thus, in this aspect of the invention, a biological sample may be treated with nitrocellulose, or other solid support which is capable of immobilizing cells, cell particles or soluble protein. The support may then be washed with suitable buffers followed by treatment with the detectably labeled ATHERO-ELAM specific antibody. The solid phase support may then be washed with the buffer a second time to remove unbound antibody. The bound label on the antibody may then be detected by conventional means.

Labeled ATHERO-ELAM specific antibody/ATHERO-ELAM complex in a sample may be separated from a reaction mixture by contacting the complex with an immobilized antibody or protein which is specific for an immunoglobulin, e.g., protein A, protein G, anti-IgM or anti-IgG antibodies. Such anti-immunoglobulin antibodies may be monoclonal or polyclonal. The solid support may then be washed with a suitable buffer to give an immobilized ATHERO-ELAM/labeled ATHERO-ELAM specific antibody complex. The label on the protein may then be detected to give a measure of endogenous ATHERO-ELAM and, thereby, the extent to which endothelial cells are expressing ATHERO-ELAM.

This aspect of the invention relates to a method for detecting ATHERO-ELAM or monocyte-binding fragment thereof in a sample comprising (a) contacting a sample suspected of containing ATHERO-ELAM with an ATHERO-ELAM specific antibody or fragment thereof which binds to ATHERO-ELAM;

(b) detecting whether a complex is formed.

The invention also relates to a method of detecting ATHERO-ELAM in a sample, further comprising (c) contacting the mixture obtained in step (a) with an Fc binding molecule, such as an antibody, protein A, or protein G, which is immobilized on a solid phase support and is specific for the ATHERO-ELAM specific antibody to give a ATHERO-ELAM/ATHERO-ELAM specific antibody-immobilized antibody complex;

(d) washing the solid phase support obtained in step (c) to remove unbound ATHERO-ELAM/ATHERO-ELAM specific antibody complex;

(e) and detecting the label on the ATHERO-ELAM specific antibody.

Of course, the specific concentrations of detectably labeled antibody and ATHERO-ELAM, the temperature and time of incubation, as well as other assay conditions may be varied, depending on various factors including the concentration of ATHERO-ELAM in the sample, the nature of the sample, and the like. Those skilled in the art will be able to determine operative and optimal assay conditions for each determination by employing routine experimentation.

One of the ways in which the ATHERO-ELAM specific antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the ATHERO-ELAM specific antibody include, but are not limited to, malate dehydrogenase, staphylococcal nuclease, delta-V-steroid isomerase, yeast alcohol dehydrogenase, alpha-glycero-phosphate dehydrogenase, triose phosphate isomerase, horse-radish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The ATHERO-ELAM specific antibody may also be labeled with a radioactive isotope which can be determined by such means as the use of a gamma counter or a scintillation counter or by autoradiography. Isotopes which are useful for the purpose of the present invention are well known in the art.

It is also possible to label the ATHERO-ELAM specific antibody with a fluorescent compound. When the fluorescently labeled antibody is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The ATHERO-ELAM specific antibody can also be detectably labeled using fluorescence emitting metals. These metals can be attached to the ATHERO-ELAM specific antibody using such metal chelating groups as diethylenetriaminepentaacetic acid (DTPA) or ethylenediaminetetraacetic acid (EDTA).

The ATHERO-ELAM specific antibody also can be detectably labeled by coupling it to a chemiluminescent compound. The presence of the chemiluminescent-tagged ATHERO-ELAM specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the ATHERO-ELAM specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the ATHERO-ELAM specific antibody may be accomplished by gamma scintillation counters, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate to similarly prepared standards.

Expression of ATHERO-ELAM can be detected using immunoglobulins, or fragments thereof, capable of recognizing and binding to the antigen. Furthermore, the antibodies may be labeled to permit their detection following administration to a mammal. The immunoglobulins can be polyclonally or monoclonally derived.

If desired, polyclonal immunoglobulin preparations may be prepared from the blood of immunized individuals of the desired species following immunization with ATHERO-ELAM followed by harvesting of the blood and processing it according to defined techniques. A distinct advantage of non-specific, polyclonal immunoglobulin preparations is that by preparing immunoglobulin from the same species into which it will be injected, immune reactions across species barriers are prevented and repeated injections of the same product are less likely to cause side-effects.

Monoclonal immunoglobulins which can be used according to the method of the invention can be prepared using hybridoma fusion techniques (Kohler et al., *European Journal of Immunology* 6:292, 1976) or can be derived from known secreting myeloma cell lines such as those available from depositories such as the American Type Culture Collection.

In detecting early atherosclerotic development in an individual, the detectably labeled immunoglobulin is advantageously given in a dose which is diagnostically effective. The term "diagnostically effective" means that the amount of detectably labeled immunoglobulin administered is sufficient to enable detection of the site of the atherosclerotic plaque when compared to the background signal.

Generally, the dosage of detectably labeled immunoglobulin for diagnosis will vary depending on considerations such as age, condition, sex, and extent of disease in the patient. The dosage will also depend on counterindications, if any, and other variables, to be adjusted by the individual physician. Dosage can vary from 0.01 mg/kg to 2,000 mg/kg, preferably 0.1 mg/kg to 1,000 mg/kg.

The term "immunoglobulin or a fragment thereof" as used herein is meant to include intact molecules as well as fragments thereof, such as, for example, the Fab and $F(ab)_2$ fragments, which are capable of binding to antigenic determinants of the graft tissue.

The term "diagnostically labeled" means that the immunoglobulin has attached to it a diagnostically detectable label.

There are many different labels and methods of labeling known to those of ordinary skill in the art. Examples of the types of labels which can be used in the present invention include radioactive isotopes and paramagnetic isotopes.

Those of ordinary skill in the art will know of other suitable labels for binding to the immunoglobulins used in the invention, or will be able to ascertain such, using routine experimentation. Furthermore, the binding of these labels to the immunoglobulin can be done using standard techniques common to those of ordinary skill in the art.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140-200 keV range, which may be readily detected by conventional gamma cameras.

For in vivo diagnosis, radionuclides may be bound to immunoglobulin either directly or indirectly by using an intermediary functional group. Intermediary functional groups which are often used to bind radioisotopes which exist as metallic ions to immunoglobulins are diethylenetriaminepentaacetic acid (DTPA) and ethylenediaminetetraacetic acid (EDTA).

The immunoglobulins used in the method of the invention can also be labeled with paramagnetic isotopes for purposes of in vivo diagnosis. Elements which are particularly useful (as in Magnetic Resonance Imaging (MRI) techniques) in this manner are known to those of skill in the art.

This invention also relates to therapeutic uses for ATHERO-ELAM. In one embodiment, ATHERO-ELAM, or a monocyte-binding fraction thereof, may be administered to a patient to prevent adhesion of monocytes to endothelial tissue. Thus, ATHERO-ELAM, or a monocyte-binding fragment thereof, would prevent monocyte adhesion to endothelial cells which have undergone changes characteristic of the early stages in atherosclerotic lesion development.

In one embodiment, a soluble form of ATHERO-ELAM may be administered. By "soluble form" is meant an ATHERO-ELAM molecule in which the transmembrane and cytoplasmic domains are deleted. The soluble form can be obtained by expression in a host cell of a genetic construct encoding a soluble form of ATHERO-ELAM.

Monoclonal antibodies to ATHERO-ELAM may also be administered to block monocyte adhesion sites of endothelial cells expressing ATHERO-ELAM. These cells may be present in early atherosclerotic lesions, and subsequent progression of the lesions is prevented by blocking monocyte adhesion in the lesions.

The ATHERO-ELAM molecule, or fragment thereof, or antibodies and antibody fragments directed to ATHERO-ELAM, can be formulated into pharmaceutically useful compositions according to known methods, such as by admixture with a pharmaceutically acceptable carrier vehicle. In order to form a pharmaceutically acceptable composition suitable for effective administration, such compositions will contain a therapeutically effective amount of the ATHERO-ELAM, soluble form of ATHERO-ELAM, fragment of ATHERO-ELAM, or antibody or antibody fragment directed to ATHERO-ELAM, either alone or with a suitable amount of carrier vehicle.

When used for the prevention of monocyte adhesion to endothelial cells, the pharmaceutical composition may comprise from 1 pg/kg to 10 mg/kg of ATHERO-ELAM, a soluble form of ATHERO-ELAM, or fragment of ATHERO-ELAM, although higher or lower doses are possible.

An antibody directed to ATHERO-ELAM may be conjugated with a drug to treat the atherosclerotic lesion. Examples of drugs useful for this purpose are anti-proliferative, anti-coagulant, anti-oxidant and anti-inflammatory drugs.

Additional pharmaceutical methods may be employed to control the duration of action. Controlled release preparations may be achieved by the use of polymers to complex or absorb the ATHERO-ELAM, ATHERO-ELAM fragment or antibody or antibody fragment directed to ATHERO-ELAM. Controlled delivery may be achieved by selecting appropriate macromolecules (for example, polyesters, polyamino acids, polyethylene glycol, polyvinyl pyrrolidone, ethylenevinylacetate, methylcellulose, carboxymethylcellulose, protamine sulfate, or lactide/glycolide copolymers). The rate of drug release may also be controlled by altering the concentration of such macromolecules. Another possible method for controlling the duration of action comprises incorporating the therapeutic agents into particles of a polymeric substance such as polyesters, polyamino acids, hydrogels, polylactide/glycolide copolymers, or ethylenevinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system, for example, liposomes, albumin microspheres, microemulsions, nanoparticles, nanocapsules, or in macroemulsions.

ATHERO-ELAM, a soluble form of ATHERO-ELAM, a fragment of ATHERO-ELAM, or an antibody or antibody fragment directed to ATHERO-ELAM may be provided to a patient by means well known in the art. Such means of introduction include oral means, intranasal means, subcutaneous means, intramuscular means, intravenous means, intra-arterial means, or parenteral means.

Having now generally described this invention, the same will be better understood with reference to certain specific examples which are included herein for purposes of illustration only, and are not intended to be limiting of the invention, unless specified.

EXAMPLE 1

Isolation and Culture of Rabbit Endothelium

Rabbit aorta (Ao) and inferior vena cava (IVC) endothelial cells (EC) were isolated with 0.2% or 0.4% collagenase (type I, Worthington Biochem. Corp.) respectively, from everted vessels (Cybulsky, M. I., et al., *FASEB J.* 2:A1603 (1988); Danthuluri, N. R., et al., *Am. J. Physiol.* 255 (*Heart Cir. Physiol.* 24):H1549–H1553 (1988)). EC were cultured on gelatin-coated tissue culture plastic in Medium 199 (Hank's salts) containing 20% fetal bovine serum (FBS), 10–20 µg/ml EC mitogen (Biomedical Technologies Inc.) and 20–40 µg/ml porcine intestinal heparin (Sigma, grade I). EC were subcultured with Trypsin/EDTA according to standard protocols.

EXAMPLE 2

Isolation, Purification, Characterization and Labeling of Rabbit Leukocytes

Rabbit leukocytes are isolated from blood obtained from the central ear artery of donor rabbits. Erythrocytes are sedimented with 1% hydroxyethyl cellulose and platelets are separated from the leukocyte-rich plasma by centrifugation. Leukocytes in the pellet are resuspended in HBSS without divalent cations with 1% human albumin USP (American Red Cross). Neutrophils (and eosinophils, which are dense cells) are separated from mononuclear leukocytes by density gravity centrifugation (Cybulsky, M. I., et al., *Am. J. Pathol.* 125:1 (1986)). Their purity is assessed by Wright's-Giemsa staining of cytospins.

Monocytes constitute 15–30% of mononuclear cells. They are larger than lymphocytes and are isolated by elutriation according to standard protocols (Doherty, D. E., et al., *Lab. Invest.* 59:200 (1988)). The purity of monocyte preparations are assessed by nonspecific esterase staining (Yam, L. T., et al., *Amer. J. Clin. Pathol.* 125:1 (1986)) of cytospins. A purity of 85–95% and recovery of 50–80% are achieved by this method.

T lymphocytes (the predominant lymphocytes in blood) are purified by removing B lymphocytes using a panning procedure. This procedure involves adsorbing antibodies directed against rabbit immunoglobulins to plastic dishes and incubating elutriated lymphocytes for 1 hour at 4° C. B lymphocytes, which express immunoglobulins on their surface, are bound by the adsorbed antibodies. Nonadherent T cells are collected and their purity assessed by immunostaining with a MAb to rabbit T cells (L11/135, from ATCC). A nylon wool purification step (Julius, M. H., et al., *Eur. J. Immunol.* 3:645 (1973)) is utilized if necessary.

Rabbit leukocytes are labeled by the fluorescent pH indicatory probe BCECF (Molecular probes). Cells suspended at $10^7$/ml are incubated in a protein-containing buffer for 15–30 minutes (37° C.) with BCECF/AM (10–20 µM). The acetoxymethyl ester form of BCECF is permeable to cells and once in the cytoplasm it is trapped after being hydrolysed by esterase enzymes. When quantitating adherent BCECF-labeled leukocytes, the pH of the lysis buffer is adjusted to the optimum for BCECF fluorescence (pH 8.8).

Rabbit leukocytes are also labeled with $Na_2^{51}CrO_4$ or $^{111}In$ according to standard protocols (Cybulsky, M. I., et al., *Am. J. Pathol.* 125:1 (1986); Danpure, H. J., et al., *Brit. J. Radiol.* 55:247 (1982)).

EXAMPLE 3

In Vitro Adhesion Assays

Quantitative microtiter plate adhesion assays are performed according to Luscinskas et al. (Luscinskas, F. W., et al., *J. Immunol.* 142:2257 (1989)). Briefly, BCECF-labeled U937 leukocytes cells suspended in RPMI+1% FBS ($2 \times 10^5$ cells/0.2 ml/well) are allowed to adhere to confluent EC monolayers (passage 2 or 3) for 10 minutes at 37° C., then wells are filled with buffer, plates sealed, inverted, and centrifuged at 250×g for 5 minutes. Adherent leukocytes are solubilized with 0.1% SDS in 50 mM Tris-HCl pH 8.8, fluorescence quantitated in an automated plate reader (Pandex, Baxter Healthcare Corp.), and the number of leukocytes adhered in each well calculated. The relatively short adhesion time (10 minutes) is chosen in order to focus on leukocyte adhesion, rather than their transmigration under the EC monolayer, which occurs with lengthy incubations.

For adhesion inhibition assays, EC monolayers are pre-incubated for 30 minutes, 22° C., with saturating concentrations of MAb F(ab')$_2$ fragments. The concentration of F(ab')$_2$ fragments required for maximal surface binding is determined for each MAb in fluorescent immunoassays and will be in the approximate range of 10–25 µg/100 µl/well.

EXAMPLE 4

Monoclonal Antibody Techniques a) MAb Production (Immunizations, Fusions, Screening, Cloning): Mice are immunized with rabbit endothelium activated with LPS or other appropriate stimuli. Hybridomas are produced by fusing spleen lymphocytes from immunized mice with NS-1 or P3X63-Ag8.653 murine myeloma cells using standard polyethylene glycol protocols (Kohler, G., et al., *Nature* 256:495 (1975); Goding, J. W., *Monoclonal Antibodies: Principles and Practice*, 2nd ed., Academic Press, London (1986)). The fusion is plated into four 96 well microtiter plates and after approximately 2 weeks, the primary screen, a cell surface fluorescent immunoassay, is performed. This screen (see Example 5) identifies wells containing immunoglobulins which recognize LPS-upregulated antigens on rabbit endothelium, typically up to 15 wells per fusion. The hybridomas in these wells are cloned by the limiting dilution technique (Goding J. W., *Monoclonal Antibodies: Principles and Practice*, 2nd ed., Academic Press, London (1986) and then secondary screens are performed. These include adhesion blocking assays with U937 cells and immunohistochemical staining of aortas from cholesterol-fed of WHHL rabbits.

b) *Immunoglobulin production in ascites, purification and F(ab')2 production*: Immunoglobulins are produced in murine ascites (100 mg-1 g quantities), purified by ammonium sulfate precipitation, followed by ABx (Baker) chromatography according to standard methods (Goding, J. W., *Monoclonal Antibodies: Principles and Practice*, 2nd ed., Academic Press, London (1986); Nau, D. R., *BioCromatography* 4:4 (1989)). Purified immunoglobulins are digested with pepsin to F(ab'2) fragments at the optimum enzyme concentration and pH (Lamoyi, E., et al., *J. Immunol. Methods* 56:235 (1983); Parham, P., *J. Immunol.* 131:2895 (1983)).

EXAMPLE 5

Fluorescence Immunoassays

Cell surface binding assays are performed at 4° C. on viable confluent EC monolayers utilizing saturating concentrations of MAb supernatants, followed by fluorescein-conjugated F(ab'2) goat anti-murine IgG (Caltag Labs). Fluorescence levels are determined using an automated plate reader (Pandex) and specific MAb binding calculated by subtracting fluorescence readings obtained with IgG$_1$ antibodies which do not bind to rabbit EC (approximately 50 relative fluorescence units).

EXAMPLE 6

Biochemical Techniques a) Immunoprecipitations: EC proteins are biosynthetically labeled with $^{35}$S-L-cysteine and $^{35}$S-L-methionine for 5 hours (2–6 hours of LPS treatment) (Bevilacqua, M. P., et al., *Proc. Natl. Acad. Sci. USA:* 84:9238 (1987)). Surface EC proteins are labeled with $^{125}$I using a glucose oxidase/ lactoperoxidase protocol (Hubbard, A. L., et al., *J. Cell Biol.* 64:438 (1975)). EC are lysed in 100 mM Tris-HCl (pH 7.4), 150 mM NaCl, 5 mM EDTA, 1 mM phenylmethysulfonyl fluoride and 0.3% CHAPS, and insoluble material is removed by centrifugation (12,000×g, 0.5 hours, 4° C.). In immunoprecipitations, EC lysates (approximately $5 \times 10^5$ cells in 100 µl lysate/lane) are incubated for 2–4 hours (4° C.) with 100 µl of MAb culture supernatant and subsequently for 2–4 hours with goat anti-murine IgG coupled to Sepharose-4B (Cappel). The Sepharose is pretreated with unlabeled lysates to diminish nonspecific adherence of labeled proteins. Lysates of biosynthetically labeled EC, also, are precleared with a nonbinding MAb. Antigens specifically bound to Sepharose beads are extensively washed, and subjected to reduced SDS-PAGE analysis on 5–12% linear gradient gels (Laemmli, U. K., *Nature* 227:680 (1970)).

b) Radioiodination of Proteins: F(ab'2) fragments are iodinated by the lactoperoxidase method (Marchalonis, J. J., *Biochem. J.* 113:299 (1969)). Following iodination and removal of free iodine by gel filtration chromatography, their ability to bind to an endothelial target is compared to an aliquot which was not iodinated. Alternative labeling protocols, for example, the Bolton-Hunter method (Bolton, A. E., et al., *Biochem. J.* 133:529 (1973)), may also be used.

EXAMPLE 7

Morphologic Techniques a) Immunohistochemistry: Immunoperoxidase staining is performed on 4–6 µm frozen sections, fixed at −20° C. for 5 minutes in acetone or 1:1 acetone:methanol. Sections are incubated (22° C.) in succession with MAb (2 hours), biotinylated horse anti-murine IgG (1 hour) and avidin-biotin peroxidase complexes (45 minutes) (Vector Labs). Peroxidase is visualized with 3-amino-9-ethylcarbazole (Sigma) and sections counterstained with Gill's hematoxylin.

b) Staining with Oil Red 0: Lipids in aortic tissues are stained with oil red 0, an inert oil-soluble bis-azo dye, according to Adams and Bayliss (Adams, C. W. M., et al., in *Techniques of Biochemical and Biophysical Morphology*, Vol. 2, Glick, D., et al. (eds.), Wiley, New York, p. 99 (1975)). After rinsing aortas with 70% isopropyl alcohol, they are stained for 30 minutes with a filtered saturated solution of oil red 0 in 60% isopropyl alcohol, then briefly rinsed with alcohol and rehydrated.

c) Staining with Silver Nitrate: Interendothelial regions of aortic segments are stained with silver nitrate according to the protocol of Poole et al. (Poole, J. C. F., et al., *J. Pathol. Bacteriol.* 75:133 (1958)).

d) Scanning Electron Microscopy: Aortas are perfused with Hanks balanced salt solution, to remove blood, then perfusion-fixed in situ under physiologic pressure (100 mm Hg, 15 minutes) with buffered 2.5% glutaraldehyde. After harvesting, dissection of adventitia, and further fixation, portions of aorta are dehydrated with ethanol, critically-point dried, mounted on aluminum stubs and sputter-coated using a gold target according to standard protocols. Specimens are viewed in a scanning electron microscope.

EXAMPLE 8

Molecular Biologic Techniques a) Lambda qt11 cDNA Library Construction: For oligomer-primed libraries, mRNA is purified by a second round of oligo(dT) chromatography. The mRNA is converted to double-stranded cDNA by the method of Okayama and Berg (Okayama, H., et al., *Mol. Cell Biol.* 2:161 (1982)) as modified by Gubler and Hoffman (Gubler, U., et al., *Gene* 25:263 (1983)). Briefly, single stranded mRNA is converted to a RNA-cDNA hybrid by reverse transcriptase using a random hexanucleotide primer or oligo(dT). Next, the RNA-cDNA hybrid is converted to double stranded cDNA with a combination of RNase H (to cleave the RNA) and DNA polymerase (to synthesize the second cDNA strand using the nicked RNA as primers). Incomplete synthesis of the second cDNA strand is repaired by *E. coli* DNA ligase. Double-stranded cDNA is then protected from digestion by methylation, converted to a blunt-ended form by T4 DNA polymerase, and EcoRI linkers added. After cutting linkers with EcoRI and size selecting, cDNA's are ligated into EcoRI-cut gt11 procaryotic expression vector.

b) Oligonucleotide Synthesis: Oligonucleotides are synthesized using standard phosphoramidite chemistry (cycles of detritylation, addition, capping, oxidation and deprotection) with a DNA synthesizer, such as, for example, Applied Biosystems Model 381A.

c) Radiolabeling of Probes: Radiolabeling of cDNA probes is performed using the oligonucleotide labeling method of Feinberg and Vogelstein (Feinberg, A. P., et al., *Anal. Biochem.* 132:6 (1983)). This method utilizes random hexadeoxyribonucleotides as primers for DNA polymerase I-catalyzed DNA synthesis in the presence of $^{32}P$-labeled nucleotides. The cDNA probe, denatured cDNA templates denatured by boiling serves as a template. Oligonucleotide probes are labeled using T4 polymerase kinase to specifically transfer $^{32}P$ label from the gamma position of ATP to the 5' OH groups of oligo DNA (Sambrook, J., et al., *Molecular Cloning. A Laboratory Manual*, Cold Spring Harbor Laboratory Press, Cold Spring Harbor, N.Y. (1989)).

d) Sequencing DNA: Sequencing is performed utilizing commercially available kits according to the Sanger method of dideoxy-mediated chain termination (Sanger, F., et al., *Proc. Natl. Acad. Sci. USA* 74:5463 (1977)). SP6, T7 and oligonucleotide primers are utilized.

e) Northern Blotting: Cytoplasmic RNA is isolated by sucrose sedimentation, proteinase K digestion and phenol/chloroform extraction (Sambrook, J., et al., *Molecular Cloning. A Laboratory Manual*, Cold Spring Harbor Laboratory Press, Cold Spring Harbor, N.Y. (1989)). After spectrophotometric quantitation and analysis in minigels, RNA is electrophoresed on formaldehyde/agarose gels and transferred by capillary action to a nitrocellulose membrane. A radio-labeled probe is hybridized to membranes, washed, and bound radioactivity visualized by autoradiography (Sambrook, J., et al., *Molecular Cloning. A Laboratory Manual*, Cold Spring Harbor Laboratory Press, Cold Spring Harbor, N.Y. (1989)).

EXAMPLE 9

Inhibition of leukocyte binding to LPS-treated endothelium

After LPS treatment, EC monolayers (passage 2) were washed, then preincubated for 30 minutes (37° C. or 4° C.) with saturating concentrations of F(ab')2 (5 µg/0.1 ml RPMI 1% FBS/microtiter well). BCECF-labeled leukocytes suspended in RPMI 1% RBS ($2 \times 10^5$/0.1 ml) were added at the appropriate temperature to each well. In 37° C. adhesion assays, leukocytes were incubated for 10 minutes under static conditions with endothelium, then wells were filled with buffer, sealed, the plates inverted and centrifuged (250×g, 5 minutes). 4° C. adhesion assays were 30 minutes in duration and nonadherent leukocytes were removed by sealing and inverting the plates for 20 minutes. Leukocyte adhesion to F(ab')2-preincubated monolayers was compared to monolayers treated with control buffer (RPMI 1% FBS) and statistical significance was established using a paired T test (*=p<0.05). The means and standard deviations (triplicate measurements) are plotted (FIG. 3).

At 4° C., Rb1/9 F(ab')2 significantly inhibited the adhesion of U937, HL60, and THP-1 cell lines, as well as centrifugally elutriated human blood monocytes and lymphocytes (FIG. 3, upper panel). U937 and HL60 adhesion was also inhibited in assays performed at 37° C. Significant decreases in adhesion were not observed with Rb2/4 or Rb2/3 F(ab')2 (FIG. 3, middle and lower panels) or with W6/32 F(ab')2, a MAb which recognizes the major histocompatibility antigen on the human leukocytes, but not on rabbit EC. Adhesion to unactivated rabbit endothelium was not significantly inhibited by any of the F(ab')2 fragments. PMN adhesion to LPS-activated endothelium was not inhibited by Rb1/9 F(ab')2 under any conditions. Taken together, these data indicate that Rb1/9 recognizes a leukocyte adhesion molecule which appears to be selective for mononuclear leukocytes.

EXAMPLE 10

Immunohistochemical staining of rabbit aortas

Immunohistochemical staining was performed on aortas from rabbits fed a hypercholesterolemic diet and from Watanabe heritable hyperlipidemic (WHHL) rabbits. Specific staining with monoclonal antibody Rb1/9 was localized to endothelium covering foam-rich aortic intimal lesions, at various stages of their development.

Frozen sections of the same atherosclerotic lesion located in the descending thoracic aortic from a rabbit fed a 1% cholesterol diet for 9 weeks are shown in FIG. 4, A–D (arrowhead marks edge of lesion). In section A, the lesion was stained for smooth muscle cells with MAb CGA7 (directed to smooth muscle cell-specific alpha actin, 1/300 dil. of ascites, ENZO Biochem. Inc.). M=media, IL=intimal lesion, bar=100 µm. In section B, the lesion was stained for rabbit macrophages with MAb RAM 11 (1/3000 dil. of ascites), bar=100 µm. In sections C and D, the lesion was stained for ATHERO-ELAM with Rb1/9 (culture supernatant). ATHERO-ELAM expression was detected in EC overlying and immediately adjacent to the intimal lesion.

EC in adjacent uninvolved aorta (UA) failed to stain with Rb1/9, but did stain with a constitutive EC marker (FIG. 4, C inset, goat anti-human von Willebrand Factor, 1/3000 dil. of IgG, Atlantic Ab., bar=50 µm). In adjacent sections, EC did not stain with a nonbinding, isotype matched MAb E1/C15 (D inset, culture supernatant, bar=10 µm). FC=foam cells, IEL=internal elastic lamina, bars in FIG. 4C and 4D represent 50 and 10 µm, respectively. FIG. 4E shows Rb1/9 staining of EC overlying an intimal foam cell-rich lesion in the aortic arch of an 18-week WHHL rabbit (bar=10 µm). FIG. 4F shows focal ATHERO-ELAM expression associated with small foam cell aggregates in the descending thoracic aorta of a rabbit with dietary hypercholesterolemia (bar=100 µm).

Immunoperoxidase staining was performed on 4–6 µm frozen sections, fixed at −20° C. for 5 minutes in acetone, or 1:1 acetone:methanol (for CGA7 and RAM11). Sections were incubated (22° C.) in succession with MAb (2 hours), biotinylated horse anti-murine IgG (1 hour) and avidin-biotin peroxidase complexes (45 minutes) (Vector Labs.). Peroxidase was visualized with 3-amino-9-ethylcarbazole (Sigma) and sections were counterstained with Gill's hematoxylin. The MAb developed to rabbit EC, including Rb1/9, do not recognize epitopes on normal or activated human endothelium in culture or in tissue sections.

EXAMPLE 11

Immunoprecipitation of polypeptides with MAb Rb1/9

EC proteins were biosynthetically labeled with $^{35}$S-L-cysteine and $^{35}$S-L-methionine for 5 hours (2nd to 7th hour of LPS treatment (Luscinskas, F. W., et al., *J. Immunol.* 142:2257 (1989); Bevilacqua, M. P., et al., *Proc. Natl. Acad. Sci. USA* 84:9238 (1987); Smith, C. W., et al., *J. Clin. Invest.* 82:1746 (1988)). Surface EC proteins were labeled with $^{125}$I using a glucose oxidase/lactoperoxidase protocol (Hubbard, A. L., et al., *J. Cell. Biol.* 64:438 (1975)).

EC were lysed in 100 mM Tris-HCl (pH 7.4), 150 mM NaCl, 5 mM EDTA, 1 mM phenylmethylsulfonyl fluoride and 0.3% CHAPS, and insoluble material was removed by centrifugation (12,000×g, 0.5 hour, 4° C.). In immunoprecipitations, EC lysates (approximately 5×10$^5$ cells in 100 µl lysate/lane) were incubated for 2–4 hours (4° C.) with 100 µl of MAb culture supernatant and subsequently for 2–4 hours with goat anti-murine IgG coupled to Sepharose-4B (Cappel), which was pretreated with unlabeled lysates to diminish nonspecific adherence of labeled proteins. Lysates of biosynthetically labeled EC, also, were precleared with a nonbinding MAb. Antigens specifically bound to Sepharose beads were extensively washed, and subjected to reduced SDS-PAGE analysis on 5–12% linear gradient gels (Laemmli, U. K., *Nature* 227:680 (1970)).

Immunoprecipitation with MAb Rb1/9 and Rb2/4 showed reciprocal specific depletion of antigen. In contrast, two successive immunoprecipitations with MAb Rb2/3 did not deplete the polypeptides recognized by Rb1/9 and Rb2/4 (FIG. 5B).

N-terminal amino acid sequence derived from the purified 98K polypeptide (ATHERO-ELAM) showed 20 of 22 amino acid homology (Sequence ID 2, amino acids 1–22) to the predicted N-terminal sequence of human VCAM-1 (Sequence ID 7, amino acids 1–22) (FIG. 6). N-terminal sequences of the 118K and 98K polypeptides were identical and in Western blots both polypeptides were recognized by MAb Rb1/9, suggesting that both are products of the same gene.

The polypeptides were purified by Rb1/9 immunoaffinity chromatography (Affi-Gel Hz, Bio Rad) and SDS-PAGE from cell membrane preparations obtained from lungs of 10 rabbits sacrificed 4 hours after an intravenous LPS injection (100 µg/kg). After SDS-PAGE, the polypeptides were electrotransferred (25 mM Tris, 192 mM Glycine, pH 8.3, 20% methanol buffer, 100V, ×100 minutes, 4° C.) to an Immobilon-P membrane (Millipore Corp.), and N-terminal amino acid sequences obtained from excised Coomassie Brilliant Blue-stained bands, by phenyl isothiocyanate degradation cycles using an automated gas phase sequencer (Applied Biosystems) (LeGendre, N., et al., in *A Practical Guide to Protein and Peptide Purification for Microsequencing*, Matsudaira, P. (ed.), Academic Press, San Diego, p. 49 (1989)).

Figure 5A:
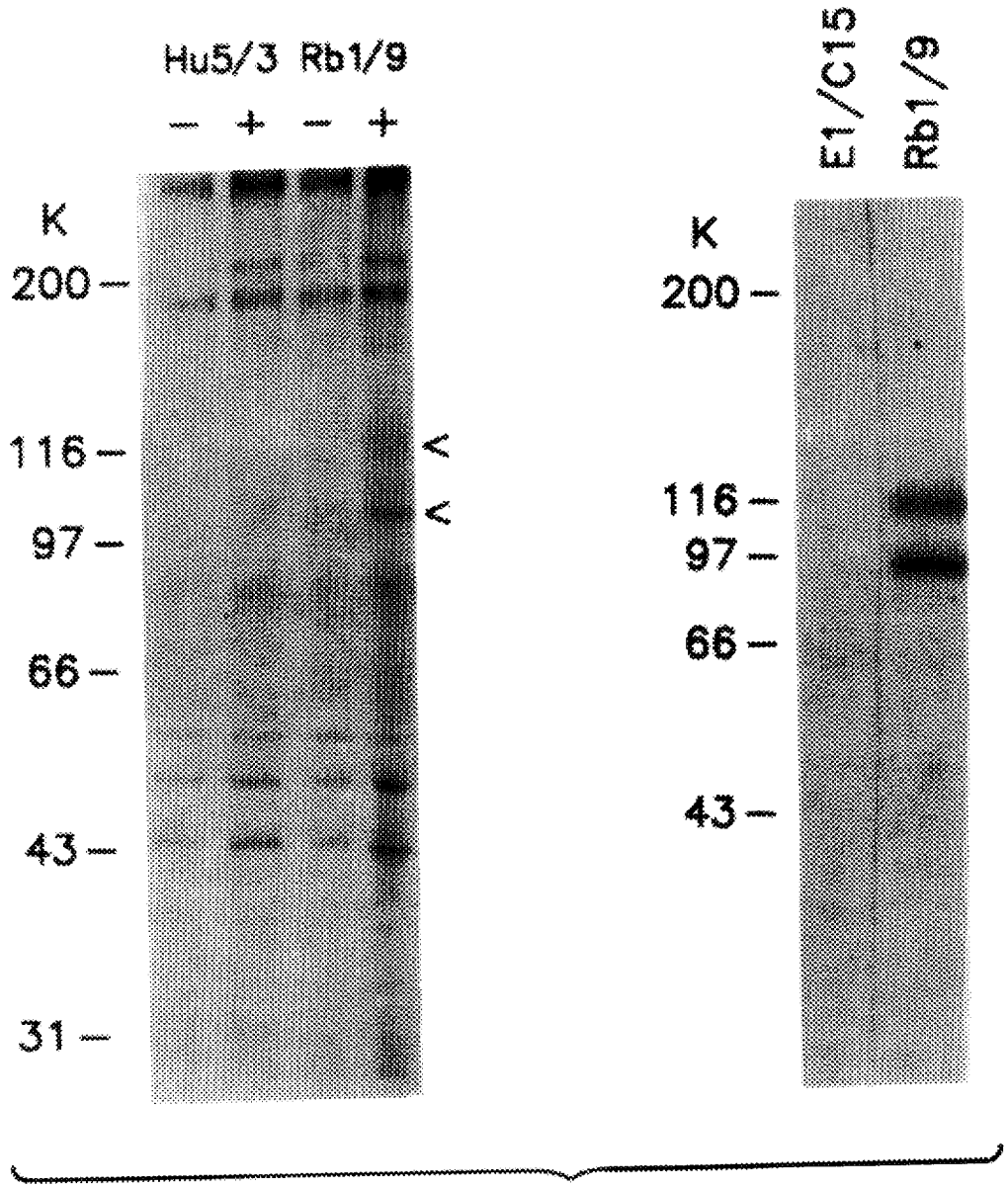
Figure 5B:
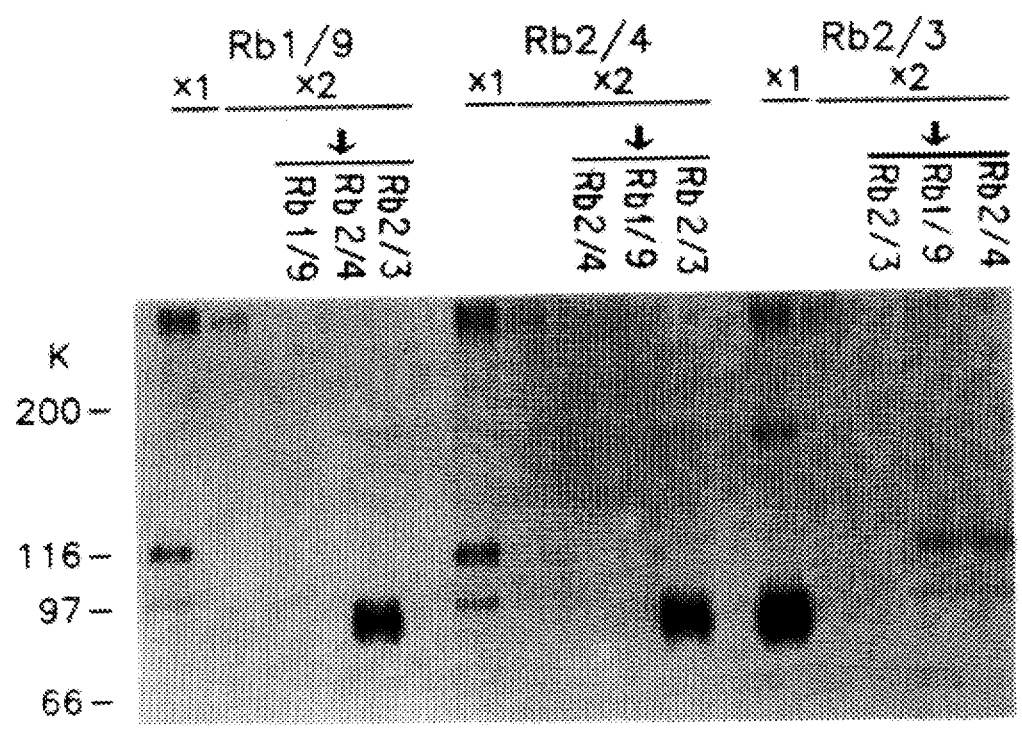

FIG. 5A shows biosynthetically labeled cells (left panel, [−]=control EC, [+]=LPS-activated), and surface-iodinated LPS-activated cells (right panel). MAb Hu5/3 and E1/C15 (IgG1) bind to human, but not rabbit, EC and did not specifically precipitate polypeptides.

EXAMPLE 12

Cell and monoclonal antibody binding to EC monolayers

Quantitative adhesion assays were performed in microtiter plates. U937 cells labeled with BCECF and suspended in RPMI 1% RBS (2×10$^5$ cells/0.2 ml/well) were allowed to adhere to EC monolayers for 10 minutes at 37° C., then wells were filled with buffer, plates sealed, inverted, and centrifuged (250×g, 5 minutes, 22° C.) (Luscinskas, F. W., et al., *J. Immunol.* 142:2257 (1989); Bevilacqua, M. P., et al., *Proc. Natl. Acad. Sci. USA* 84:9238 (1987); Smith, C. W., et al., *J. Clin. Invest.* 82:1746 (1988)).

MAb were generated by fusing NS-1 myeloma cells with spleen cells from mice immunized with 5 hour LPS-treated IVC EC according to standard protocols. Cell surface binding assays were performed at 4° C. on viable EC monolayers, utilizing saturating concentrations of MAb supernatants and fluorescein-conjugated F(ab')$_2$ goat anti-murine IgG (Caltag Labs). Fluorescence levels were determined using an automated plate reader (Pandex, Baxter Healthcare Corp.) and specific MAb binding was determined by subtracting fluorescence readings obtained with IgG$_1$ antibodies which do not bind to rabbit EC (approximately 50 relative fluorescence units).

FIG. 1 illustrates U937 adhesion (A & B) and specific MAb binding (C & D) to EC monolayers (passage 2), derived from the aorta (Ao) and inferior vena cava (IVC) of the same New Zealand White rabbit. Activation of EC with LPS (*E. coli*, 1 µg/ml) increased both U937 adhesion (A) and MAb binding (C) in a time-dependent fashion. Cycloheximide (CHX, 10 µg/ml; solid bars) coincubation, during LPS treatment (5 hour) of IVC EC, abolished the LPS-induced increase in U937 adhesion (B) and RB1/9 cell surface binding (D). CHX did not affect the integrity of EC monolayers, or the binding of MAb Rb2/13 to an abundant constitutive EC antigen, whose expression was not altered by LPS (D insert). In each graph the data points represent the means and standard deviations of quadruplicate measurements.

EXAMPLE 13

Production of Soluble ATHERO-ELAM

Soluble transmembrane proteins can be produced by genetically engineering a cDNA containing a termination codon immediately 5' of the transmembrane domain. When expressed in appropriate cells, the protein synthesized from this cDNA is secreted, and can be recovered from the culture Production of soluble ATHERO-ELAM from Rabbit Endothelium Using the Polymerase Chain Reaction:

Rabbit endothelial cells are treated with 1 µg/ml of LPS for 4–8 hours at 37° C.; cytoplasmic RNA is prepared by a detergent lysis protocol (Sambrook, J., et al., *Molecular Cloning, A Laboratory Manual*, 2nd ed. Cold Spring Harbor Laboratory, Cold Spring Harbor, N.Y., (1989)). First strand cDNA is synthesized during a 1 hour incubation (42° C., final reaction volume of 40 µl), using 1 µg of RNA as template, 50 ng of an appropriate oligonucleotide primer complementary to a sequence found in the 3' untranslated region of ATHERO-ELAM mRNA and 100 U of avian myeloblastosis virus reverse transcriptase (Molecular Genetic Resources, Tampa, Fla.).

Two rounds of PCR are performed utilizing nested primers, and 5 µl of first strand cDNA or first round PCR products as templates (Saiki, R. K., et al., *Science* 239:1350 (1988)). For the first round of PCR, 300 ng of primers are used. The 5' primer corresponds to a region 5' to the open reading frame (5' untranslated region), and the 3' primer is the same as was used for cDNA synthesis. For the second round of PCR, 150 ng of primers are used. The 5' primer still corresponds to the 5' untranslated region, but is 3' to the primer used for the first round of PCR. The 3' primer is complementary to a region immediately 5' of the transmembrane domain and contains an in frame termination codon (e.g., TAA). Primers may have genetically engineered convenient restriction enzyme sites for subcloning purposes. Preferably, both rounds of PCR are 26 cycles performed under appropriate conditions: for example, one minute of denaturing at 94° C., two minutes of annealing at 50° C., and 6 minutes of extension at 72° C. with a 40 minute extension time in the first cycle. PCR products are then analyzed by standard agarose gel electrophoresis and Southern blotting.

The prominent reaction product from a parallel set of 6 PCR reaction tubes is then pooled and purified. The ends of the PCR product are repaired with the Klenow fragment of DNA polymerase I, phosphorylated with T4 kinase, and the fragment subcloned into the HincII site of the plasmid vector pBS (Stratagene, La Jolla, Calif.). Subsequently, purified plasmid DNA is cut with appropriate restriction enzymes and the ATHERO-ELAM cDNA insert subcloned into an appropriate eukaryotic expression vector, for example, pcDNA-I (Invitrogen, San Diego, Calif.). This construct is transfected into appropriate cells, for example, COS cells.

EXAMPLE 14

Cloning and Sequencing of the Human VCAM-1Gene

A bacteriophage lambda library of human peripheral blood DNA in the vector EMBL3 (Bonthron, D. T., et al., *Proc. Natl. Acad. Sci. USA* 85:1492-1496 (1988)) was plated, nitrocellulose filters prepared according to standard procedures (Sambrook, J., et al., *Molecular Cloning, A Laboratory Manual*, 2nd edition, Cold Spring Harbor Laboratory, Cold Spring Harbor, N.Y. (1989)), and screened with a rabbit partial cDNA for VCAM-1. The cDNA probe was labeled with Klenow fragment of DNA polymerase I in the presence of hexanucleotide primers and [alpha-$^{32}$P] dCTP (Feinberg, A. P., et al., *Anal. Biochem.* 132:6-13 (1983)). Filters were incubated with the radiolabeled probe in 6× SSC, 0.5% SDS at 65° C., and washed with 0.5× SSC, 0.5% SDS at 65° C. Hybridizing bacteriophage were purified and amplified, bacteriophage DNA prepared, and restriction fragments containing the VCAM-1 gene ligated into the plasmid vector pBS (Sambrook, J., et al., *Molecular Cloning, A Laboratory Manual*, 2nd edition, Cold Spring Harbor Laboratory, Cold Spring Harbor, N.Y. (1989)).

Nucleotide sequences were determined by the dideoxynucleotide chain termination procedure with modified T7 DNA polymerase (United States Biochemical Corp., Cleveland, Ohio) and [alpha-$^{35}$S]-dATP. Oligonucleotide primers were synthesized using an oligonucleotide synthesizer (Applied Biosystems, Foster City, Calif.) and were used without purification.

EXAMPLE 15

Production of a Seven Immunoglobulin Domain Soluble Human VCAM-1

Subculture 2 human umbilical vein endothelial cells (HUVEC) isolated from two to six umbilical cords (Bevilacqua M. P., et al., *Science* 243:1160–1165 (1989)) were treated with 10 U/ml of recombinant human IL-1 beta (Biogen, Boston, Mass.) for 6 hours at 37° C.; cytoplasmic RNA was prepared by a detergent lysis protocol (Sambrook, J., et al., *Molecular Cloning, A Laboratory Manual*, 2nd edition, Cold Spring Harbor Laboratory, Cold Spring Harbor, N.Y. (1989)). First strand cDNA was synthesized during a 1 hour incubation (42° C., with a final reaction volume of 40 µl), using 1 µg of RNA as template, 50 ng of an oligonucleotide primer complementary to the sequence found in the 3' untranslated region of VCAM-1 mRNA-GGGTCATATAGTCTTGTAGAAGCACAGAAATC (Sequence ID 10) and 100 U of avian myeloblastosis virus reverse transcriptase (Molecular Genetic Resources, Tampa, Fla.).

Two rounds of PCR were performed utilizing nested primers, and 5 µl of first strand cDNA or first round PCR products as templates (Salki, R. K., et al., *Science* 239:487–491 (1988)). 300 ng of primers were used for the first round of PCR and 150 ng for the second round. A primer to the 5' untranslated region of the mRNA-GAGCTGAATACCCTCCCAGGCACACACAGGTG (Sequence ID 11) and the same 3' primer as was used in cDNA synthesis were used for first round PCR. The nested set of primers consisted of GGGTTTTTGGAACCAC-TATTTTGTCATC (Sequence ID 12) and a sequence complementary to GTTTAACACTTGATGTTCAAGGAA-GAGAAAACTAA (Sequence ID 13). The latter primer encodes a termination codon (TAA) immediately 5' of the VCAM-1 transmembrane domain.

Both rounds of PCR were 26 cycles performed under the following conditions: one minute of denaturing at 94° C., two minutes of annealing at 50° C., and 6 minutes of extension at 72° C. with a 40 minute extension time in the first cycle. PCR products (10 µl) were analyzed by standard agarose gel electrophoresis and Southern blotting (Sambrook, J., et al., *Molecular Cloning, A Laboratory Manual*, 2nd edition, Cold Spring Harbor Laboratory, Cold Spring Harbor, N.Y. (1989)).

The prominent 2.05 kb reaction product from a parallel set of 6 PCR reaction tubes was pooled and purified. The ends of the PCR product were repaired with the Klenow fragment of DNA polymerase I, phosphorylated with T4 kinase, and the fragment was subcloned into the HincII site of the plasmid vector pBS (Stratagene, La Jolla, Calif.), according to standard procedures (Sambrook, J., et al., *Molecular Cloning, A Laboratory*, 2nd edition, Cold Spring Harbor Laboratory, Cold Spring Harbor, N.Y. (1989)). The PCR insert was subcloned into pcDNA-I (Invitrogen, San Diego, Calif.) and expressed in COS cells.

It will be appreciated by those skilled in the art that various modifications can be made to the above described embodiments of the invention without departing from the essential nature thereof. It is intended to encompass all such modifications within the scope of the appended claims.

We claim:

1. A substantially purified protein comprising a mononuclear leukocyte-selective endothelial-leukocyte adhesion molecule expressed in atherosclerotic lesions having the amino acid sequence shown in Sequence ID 2, and comprising an AS-1 domain between domains 3 and 4 of said protein and wherein said protein is selected from the group consisting of:

a protein having seven immunoglobulin-like domains, and a protein having eight immunoglobulin-like domains and wherein one of said eight domains is an AS-III domain.

2. The protein of claim 1 wherein said ATHERO-ELAM has a molecular weight of approximately 118 kD on an SDS-polyacrylamide gel under reducing conditions.

3. The protein of claim 1 wherein said ATHERO-ELAM has a molecular weight of approximately 98 kD on an SDS-polyacrylamide gel under reducing conditions.

4. The protein of claim 1 wherein said protein is encoded by the nucleotide sequence as shown in Sequence ID 1.

5. A substantially purified protein comprising an AS-1 domain between immunoglobulin-like domains 3 and 4 of a mononuclear leukocyte-selective endothelial-leukocyte molecule expressed in atherosclerotic lesions, said protein lacking transmembrane and cytoplasmic domains, wherein said protein comprises the sequence between amino acids 1 and 774 in Sequence ID 2, and wherein said protein is selected from the group consisting of:

a protein having seven immunoglobulin-like domains, and a protein having eight immunoglobulin-like domains and wherein one of said domains is an AS-III domain.

* * * * *

UNITED STATES PATENT AND TRADEMARK OFFICE
CERTIFICATE OF CORRECTION

PATENT NO. : 5,708,147
DATED : January 13, 1998
INVENTOR(S) : Gimbrone, Jr. *et al.*

It is certified that error appears in the above-indentified patent and that said Letters Patent is hereby corrected as shown below:

On the title page item [75] Inventors, delete "Allston" and insert therefor --Brookline--.

In claim 2, column 41, at line 8, delete "ATHERO-ELAM" and insert therefor --mononuclear leukocyte-selective endothelial-leukocyte adhesion molecule--.

In claim 3, column 41, at line 11, delete "ATHERO-ELAM" and insert therefor --mononuclear leukocyte-selective endothelial-leukocyte adhesion molecule--.

In column 7, at line 17, delete "locally" and insert therefor --focally--.

In column 19, at line 12, delete "qt11" and insert therefor --gt11--.

In column 22, at line 10, delete "(IgG1)" and insert therefor --(IgG$_1$)--.

Signed and Sealed this

Eighteenth Day of August, 1998

*Attest:*

BRUCE LEHMAN

*Attesting Officer*    Commissioner of Patents and Trademarks